United States Patent
Iwasaki et al.

(10) Patent No.: US 11,589,817 B2
(45) Date of Patent: Feb. 28, 2023

(54) CONTACT LENS AND ACCESSORY

(71) Applicants: Sony Corporation, Tokyo (JP); Sony Semiconductor Solutions Corporation, Kanagawa (JP)

(72) Inventors: Masanori Iwasaki, Kanagawa (JP); Takayuki Hirabayashi, Tokyo (JP); Naoto Yamaguchi, Tokyo (JP); Tsukasa Yoshimura, Tokyo (JP); Masakazu Yajima, Kanagawa (JP); Fumiko Shiga, Tokyo (JP); Ken Hayakawa, Kanagawa (JP)

(73) Assignees: Sony Corporation, Tokyo (JP); Sony Semiconductor Solutions Corporation, Kanagawa (JP)

( * ) Notice: Subject to any disclaimer, the term of this patent is extended or adjusted under 35 U.S.C. 154(b) by 373 days.

(21) Appl. No.: 16/652,251

(22) PCT Filed: Aug. 7, 2018

(86) PCT No.: PCT/JP2018/029528
§ 371 (c)(1),
(2) Date: Mar. 30, 2020

(87) PCT Pub. No.: WO2019/069555
PCT Pub. Date: Apr. 11, 2019

(65) Prior Publication Data
US 2020/0237308 A1     Jul. 30, 2020

(30) Foreign Application Priority Data
Oct. 5, 2017 (JP) .............................. JP2017-195326

(51) Int. Cl.
*A61B 5/00* (2006.01)
*G02C 7/04* (2006.01)
(Continued)

(52) U.S. Cl.
CPC ............ *A61B 5/6821* (2013.01); *A61B 5/002* (2013.01); *G02C 7/04* (2013.01); *A61B 3/113* (2013.01);
(Continued)

(58) Field of Classification Search
CPC ......... A61B 5/6821; A61B 3/113; A61B 3/16; A61B 5/02007; A61B 5/02438;
(Continued)

(56) References Cited

U.S. PATENT DOCUMENTS

2014/0277291 A1* 9/2014 Pugh .................. A61B 5/14507
607/88
2016/0062150 A1   3/2016 Sako et al.
(Continued)

FOREIGN PATENT DOCUMENTS

| CN | 104069588 A | 10/2014 |
| CN | 105122121 A | 12/2015 |

(Continued)

OTHER PUBLICATIONS

International Search Report issued in International Patent Application No. PCT/JP2018/029528 dated Oct. 23, 2018, and English translation of same. 4 pages.
(Continued)

*Primary Examiner* — William R Alexander
*Assistant Examiner* — Sharrief I Broome
(74) *Attorney, Agent, or Firm* — K&L Gates LLP

(57) ABSTRACT

A contact lens according to an embodiment of the present disclosure includes: a lens section that is worn on an eyeball; an acquisition section that is provided in the lens section and acquires biological information; and an output section that outputs the biological information acquired by the acquisition section to an external apparatus to be worn on a human body. The output section has one or a plurality of coil
(Continued)

antennas extending along a front surface of the lens section, and a capacitor that is coupled to the one or the plurality of coil antennas in series or in parallel.

8 Claims, 21 Drawing Sheets

(51) Int. Cl.
    *A61B 3/113*     (2006.01)
    *A61B 3/16*     (2006.01)
    *A61B 5/02*     (2006.01)
    *A61B 5/024*     (2006.01)
    *A61B 5/11*     (2006.01)
    *A61B 5/145*     (2006.01)
    *H04B 5/02*     (2006.01)

(52) U.S. Cl.
    CPC ............. *A61B 3/16* (2013.01); *A61B 5/02007* (2013.01); *A61B 5/02438* (2013.01); *A61B 5/1103* (2013.01); *A61B 5/14507* (2013.01); *H04B 5/02* (2013.01)

(58) Field of Classification Search
    CPC ...... A61B 5/14507; A61B 5/002; G02C 7/04; H04B 5/02
    See application file for complete search history.

(56) References Cited

U.S. PATENT DOCUMENTS

2016/0166851 A1*   6/2016  Pugh ........................ A61N 5/06
                                                                                         607/88
2018/0234415 A1*   8/2018  Fukuda ................... G06F 1/163
2020/0099681 A1*   3/2020  Fukuda ............... H04L 63/0861

FOREIGN PATENT DOCUMENTS

JP        2014-180565       9/2014
WO     WO2014/181568    11/2014
WO     WO-2014199886 A1  12/2014

OTHER PUBLICATIONS

Written Opinion issued in International Patent Application No. PCT/JP2018/029528 dated Oct. 23, 2018. 3 pages.

* cited by examiner

[ FIG. 1 ]
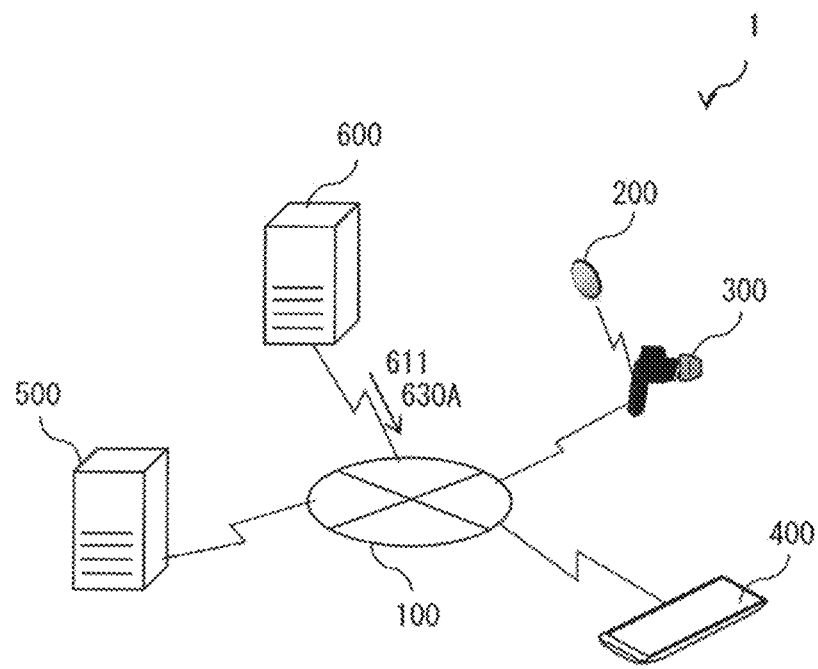
[ FIG. 2 ]
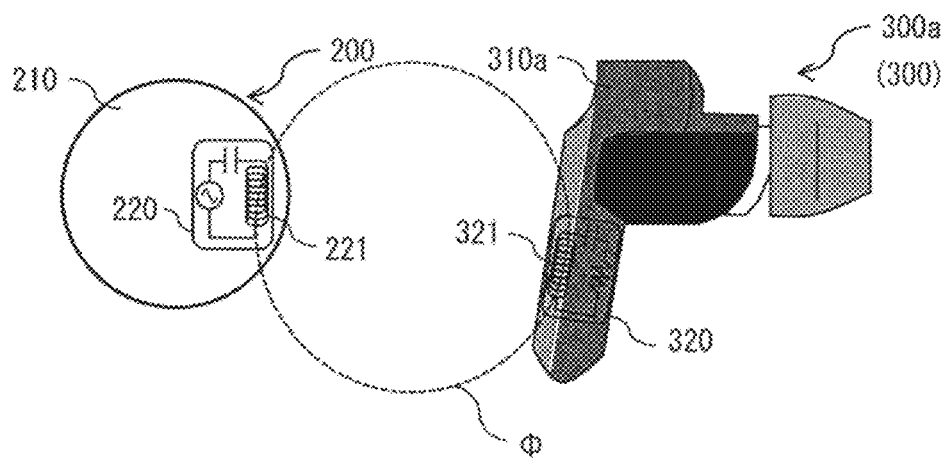

[FIG. 3]
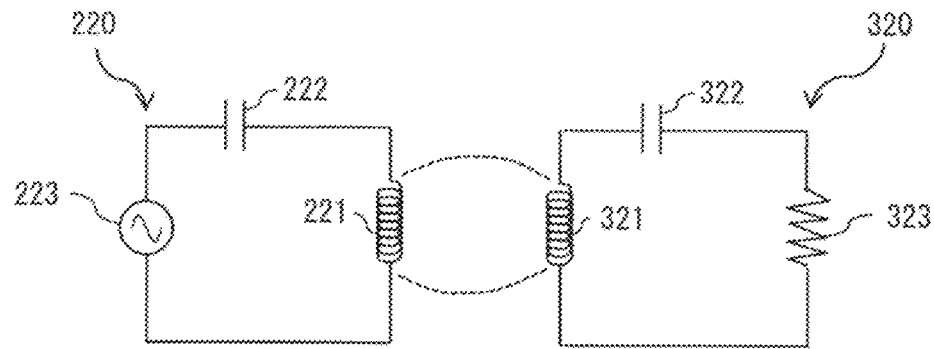
[FIG. 4]
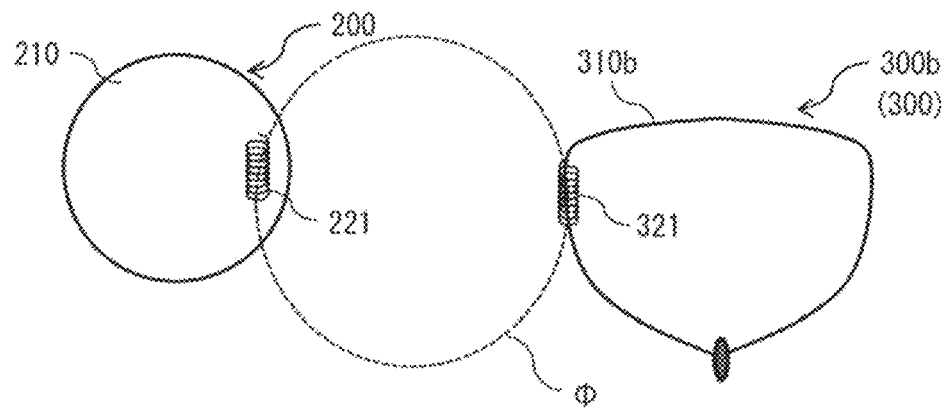
[FIG. 5]
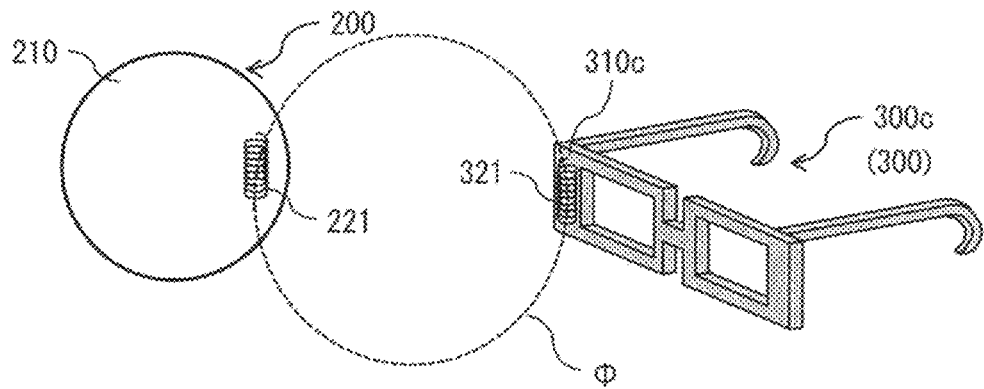

[ FIG. 6 ]
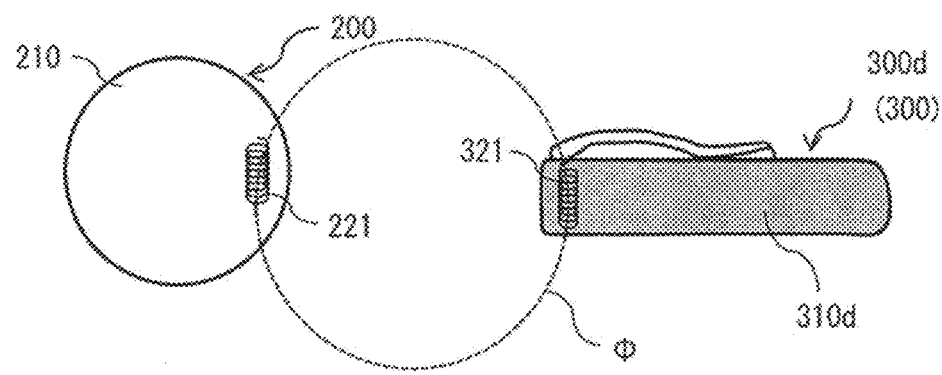
[ FIG. 7 ]
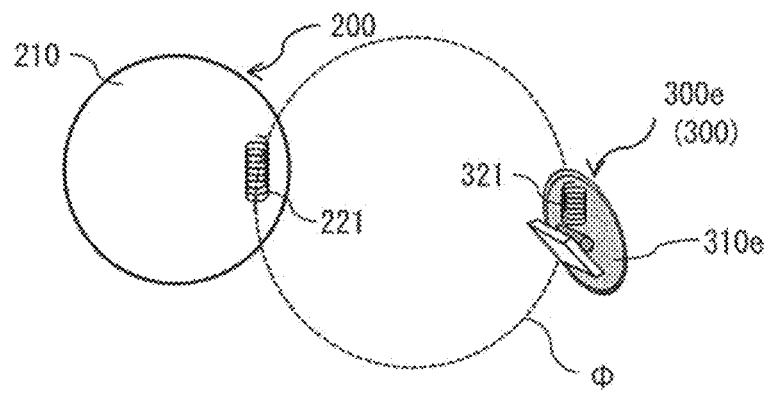
[ FIG. 8 ]
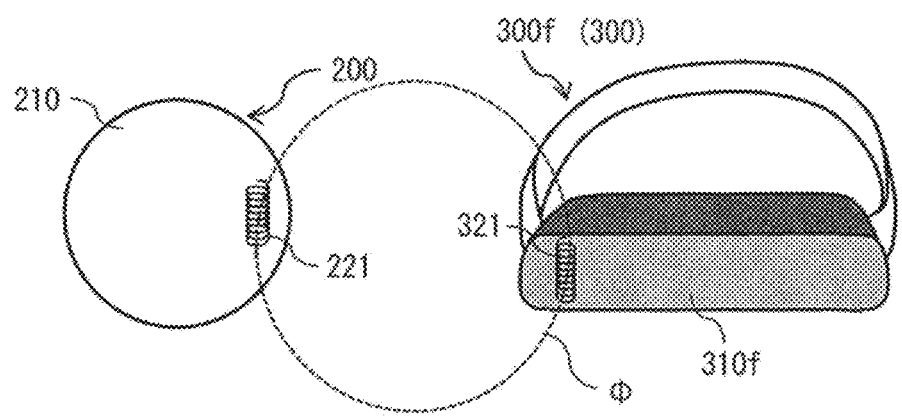

[ FIG. 9 ]
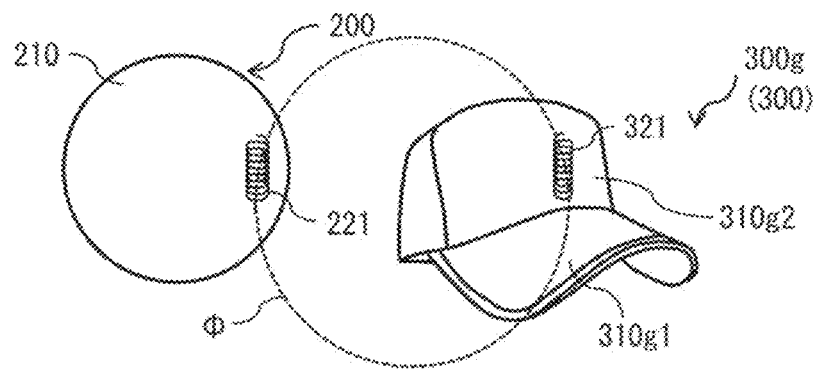
[ FIG. 10 ]
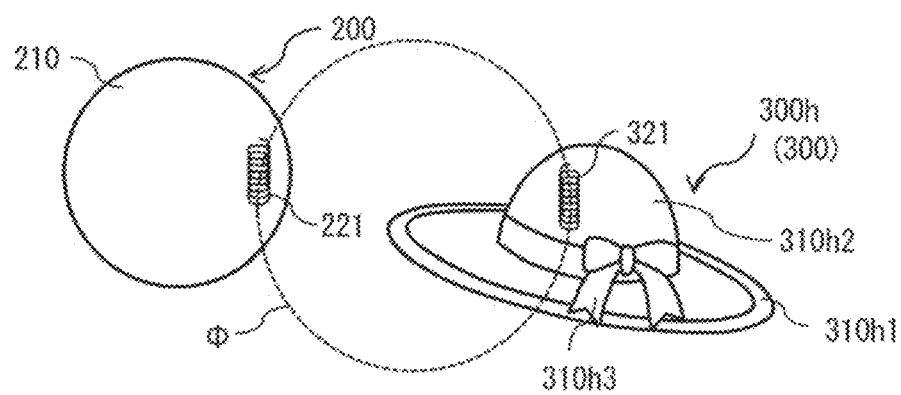
[ FIG. 11 ]
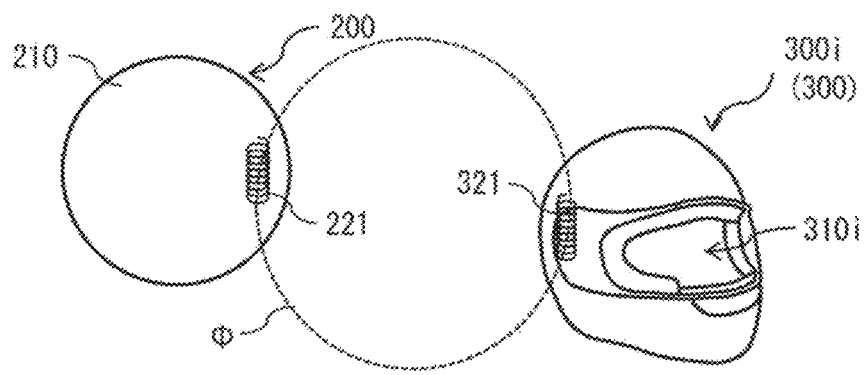

[ FIG. 12 ]
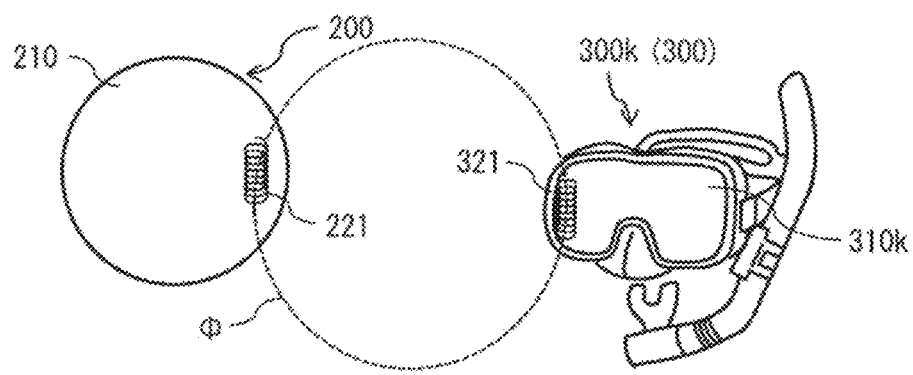
[ FIG. 13 ]
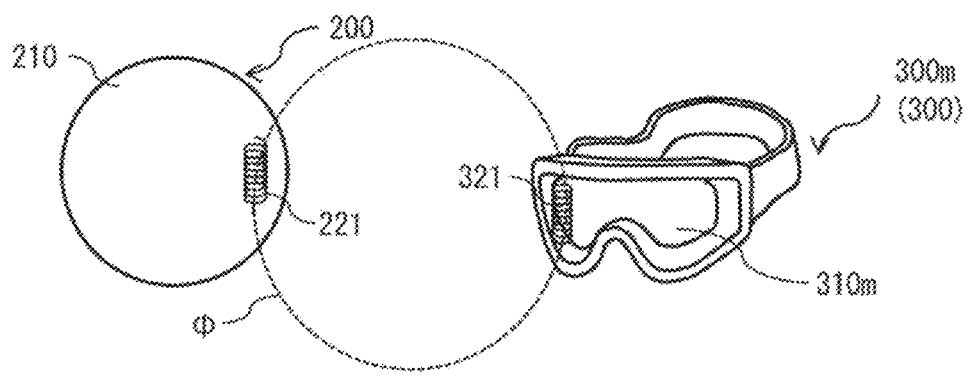
[ FIG. 14 ]
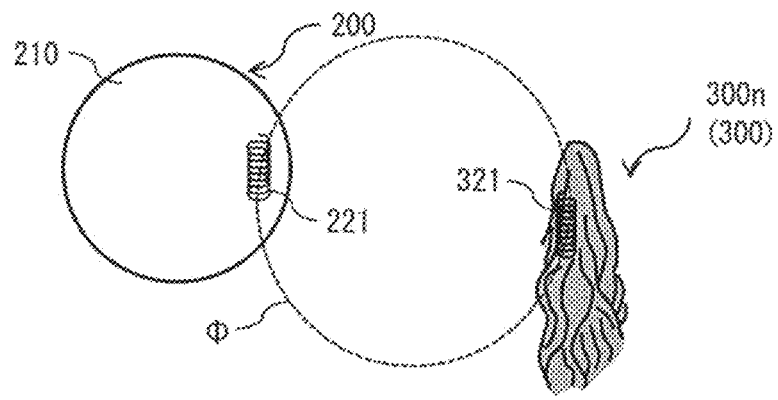

[ FIG. 15 ]
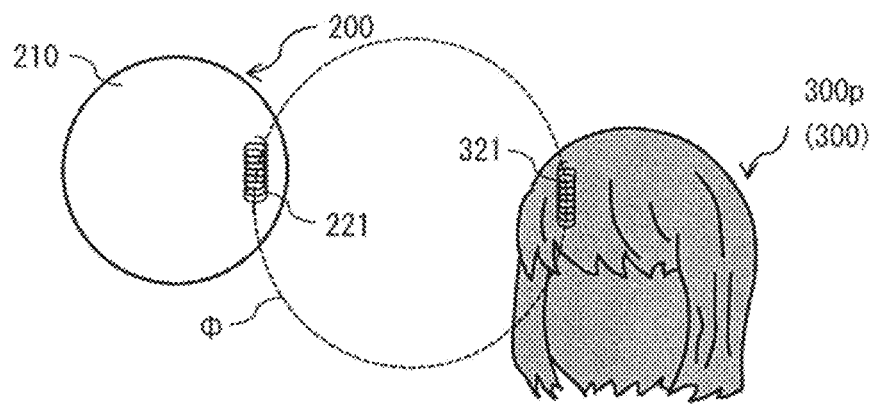
[ FIG. 16A ]
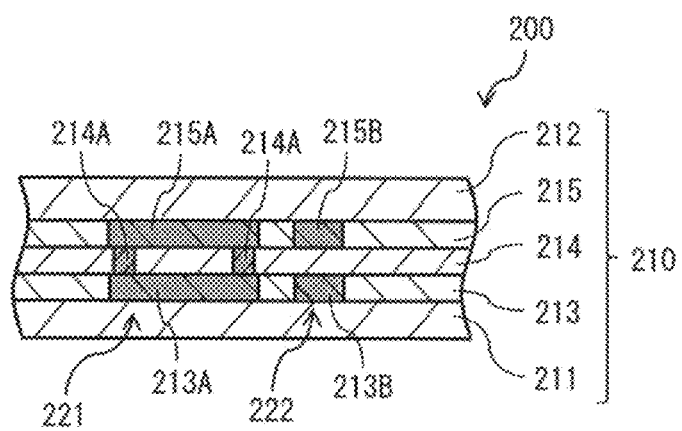

[ FIG. 16B ]
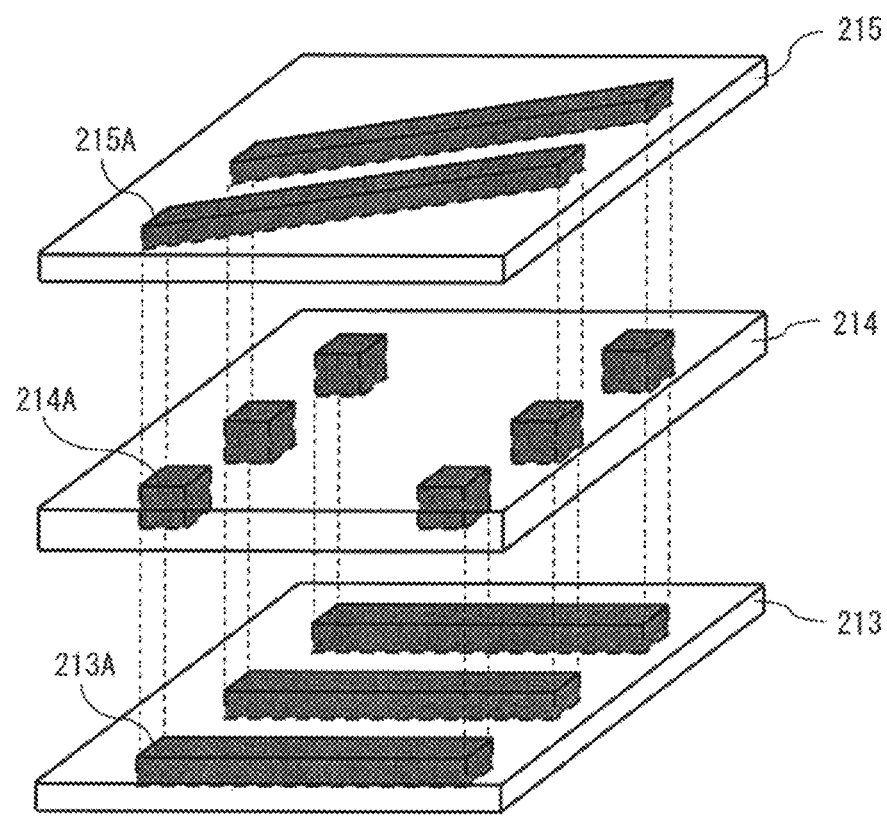
[ FIG. 17 ]
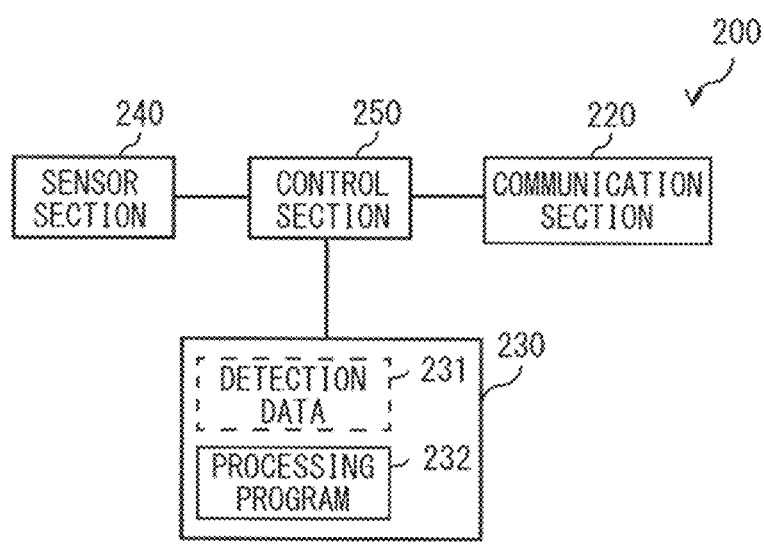

[ FIG. 18 ]
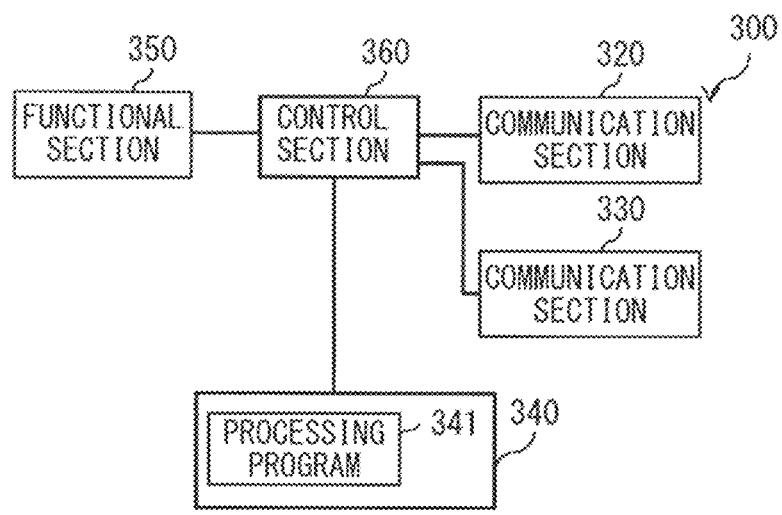
[ FIG. 19 ]
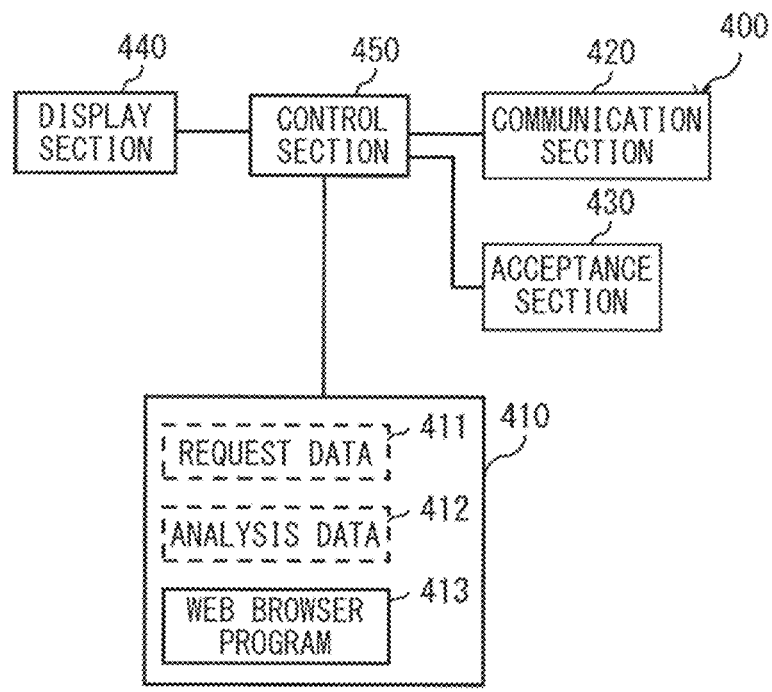

[ FIG. 20 ]
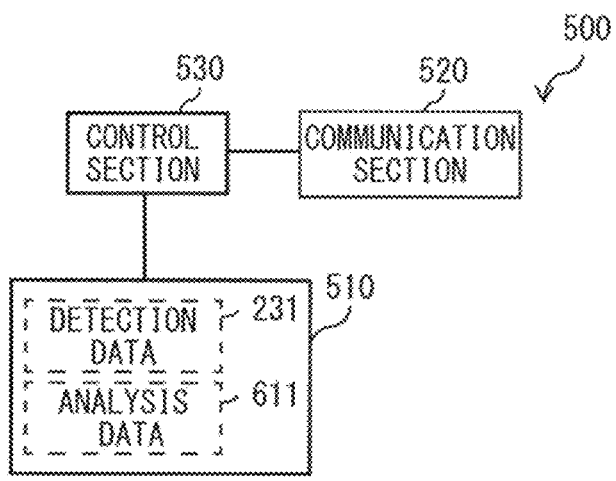
[ FIG. 21 ]
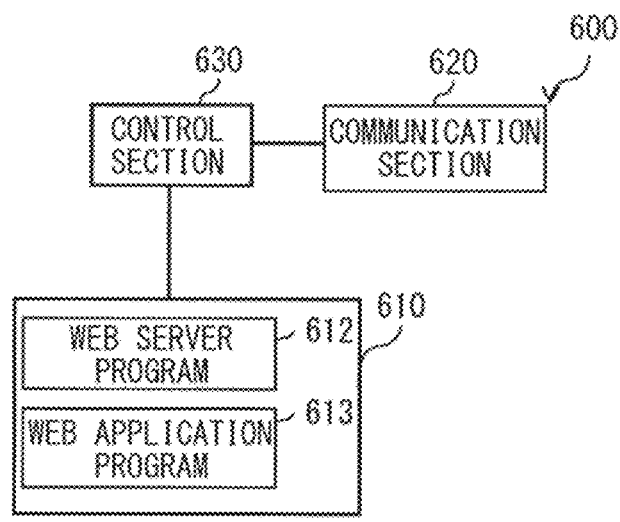

[ FIG. 22 ]
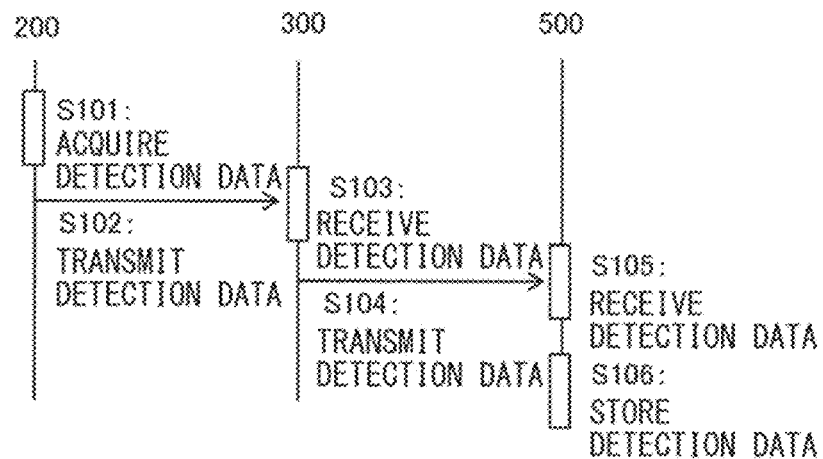
[ FIG. 23 ]
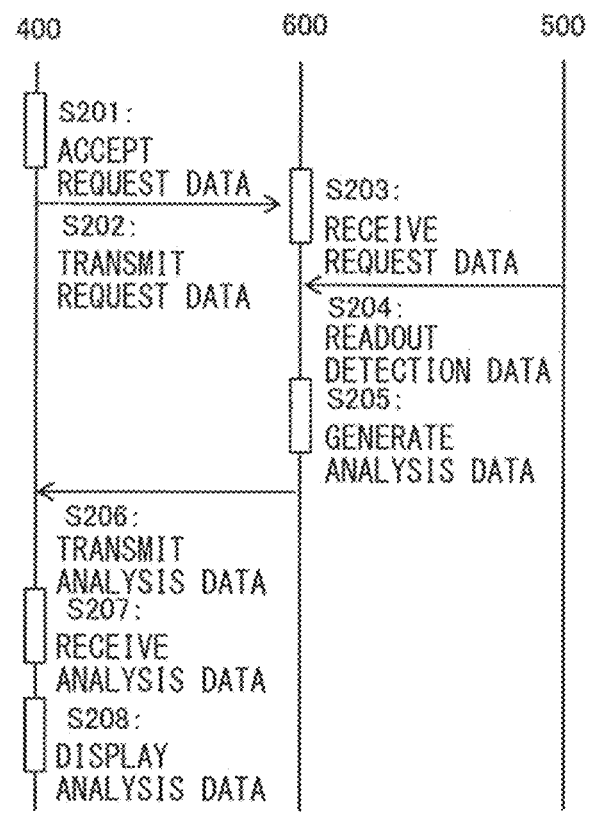

[ FIG. 24 ]
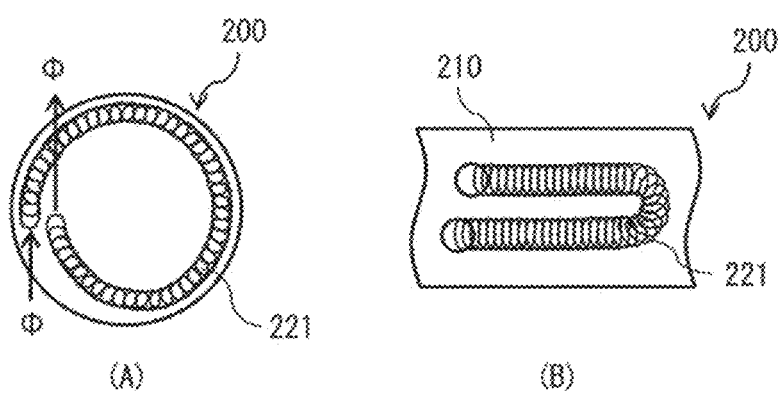
(A)    (B)
[ FIG. 25A ]
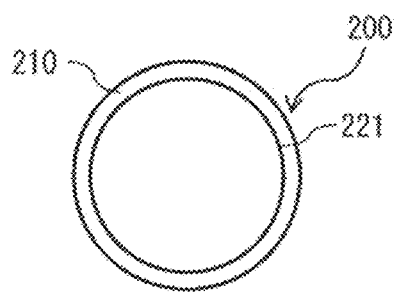

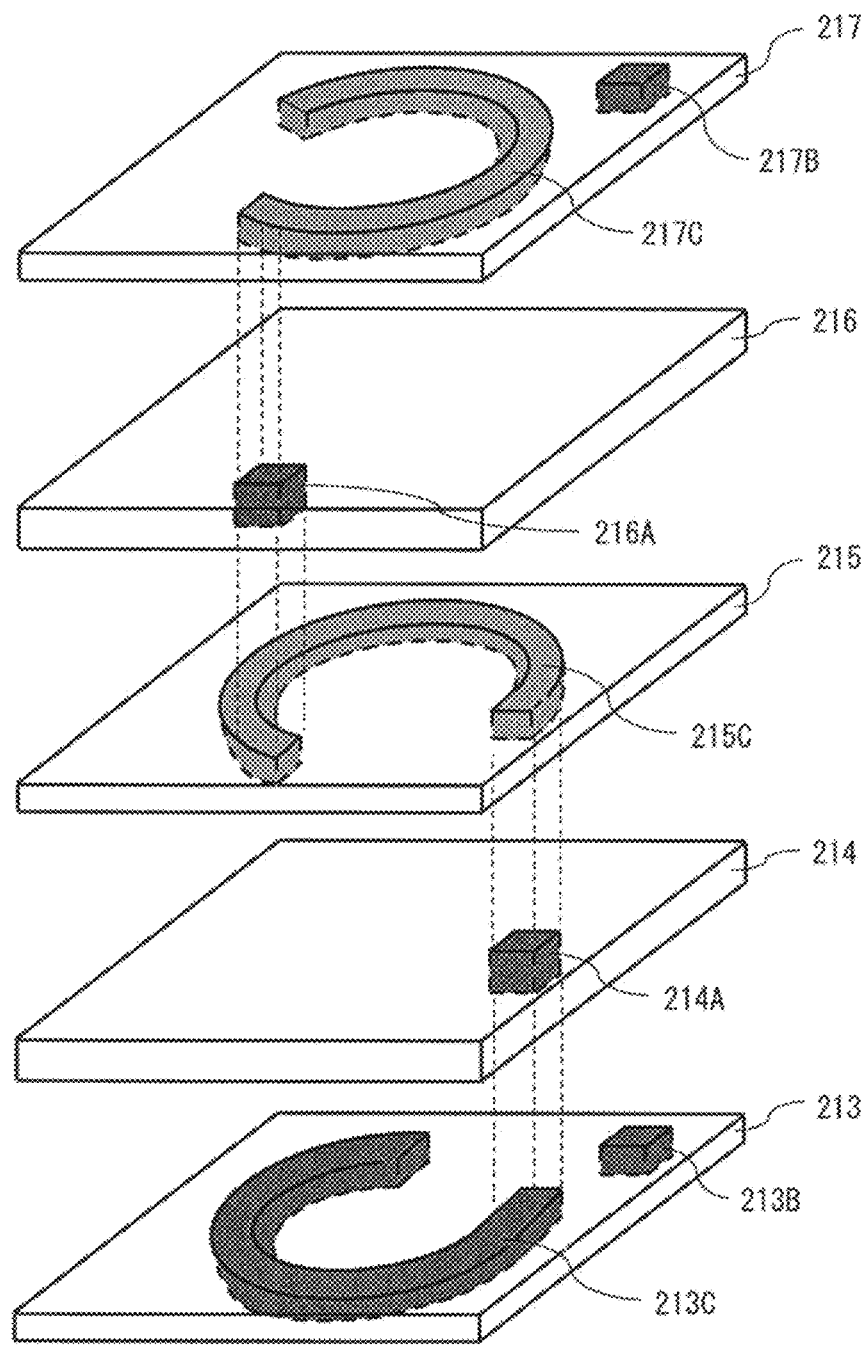
[FIG. 25B]

[ FIG. 25C ]
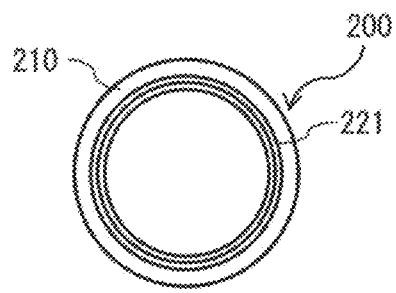
[ FIG. 26 ]
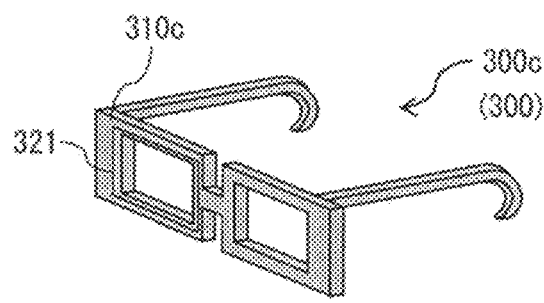
[ FIG. 27 ]
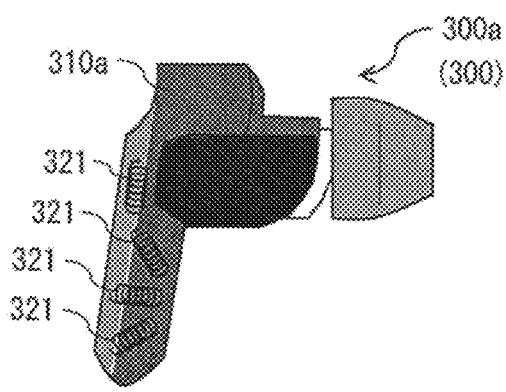

[FIG. 28]
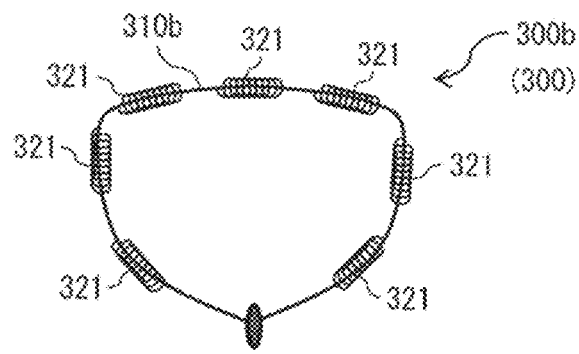
[FIG. 29]
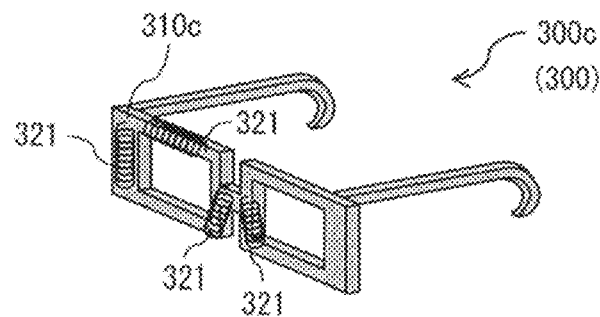
[FIG. 30]
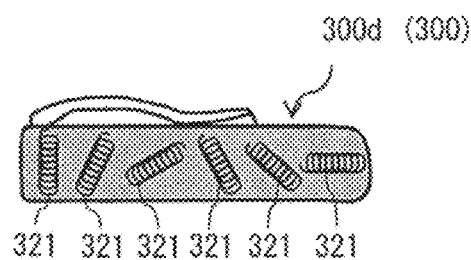
[FIG. 31]
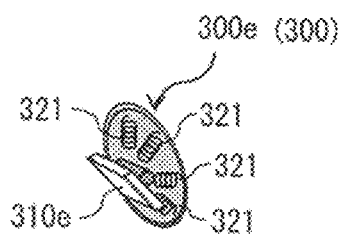

[FIG. 32]
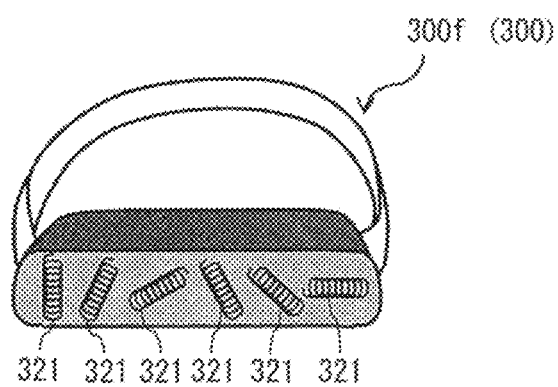
[FIG. 33]
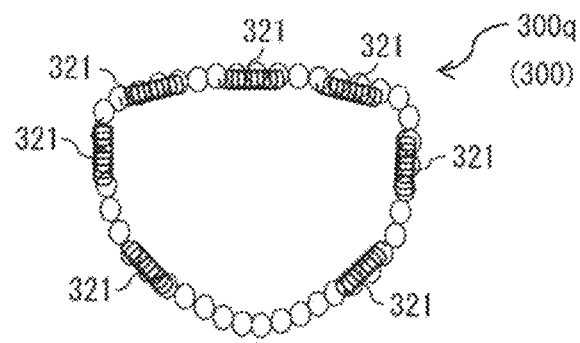
[FIG. 34]
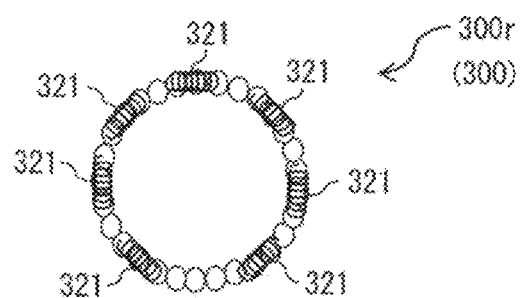

[FIG. 35]
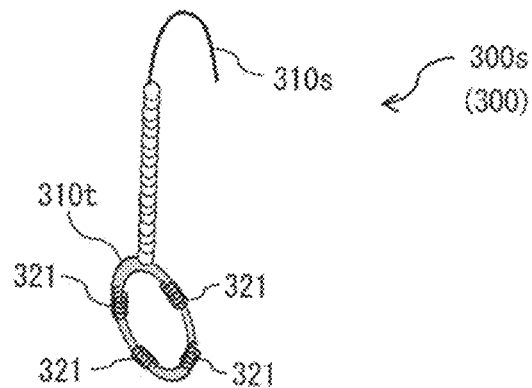
[FIG. 36]
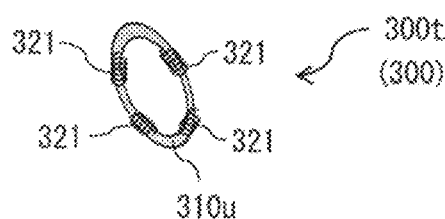
[FIG. 37]
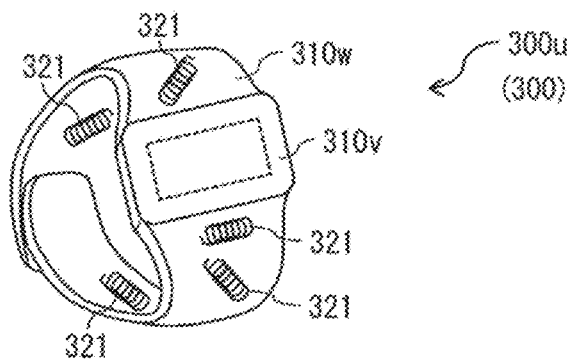

[FIG. 38]
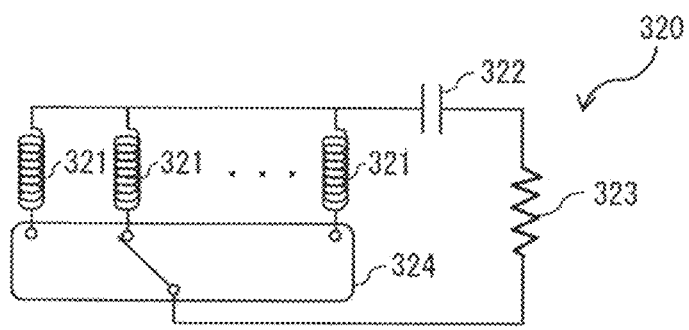
[FIG. 39]
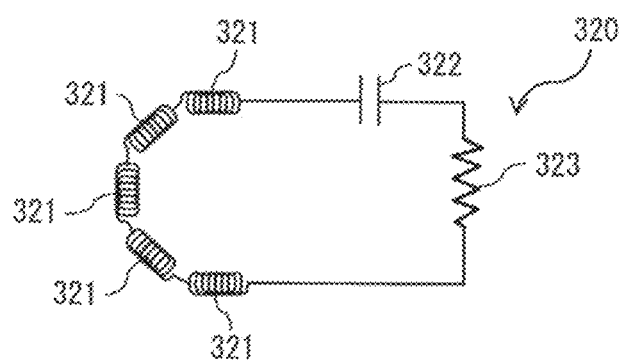
[FIG. 40]
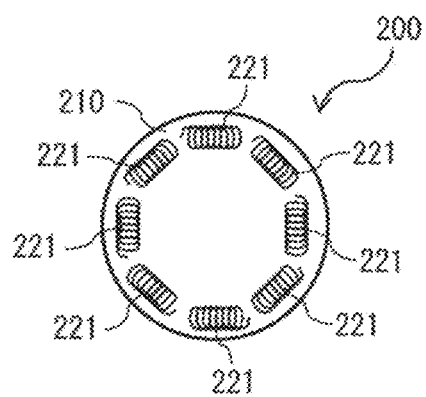

[FIG. 41]
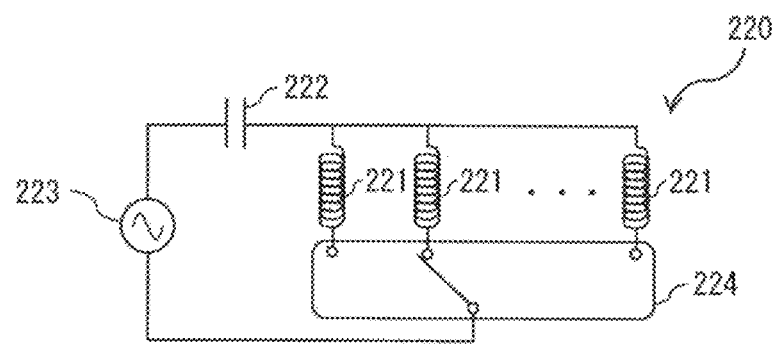
[FIG. 42]
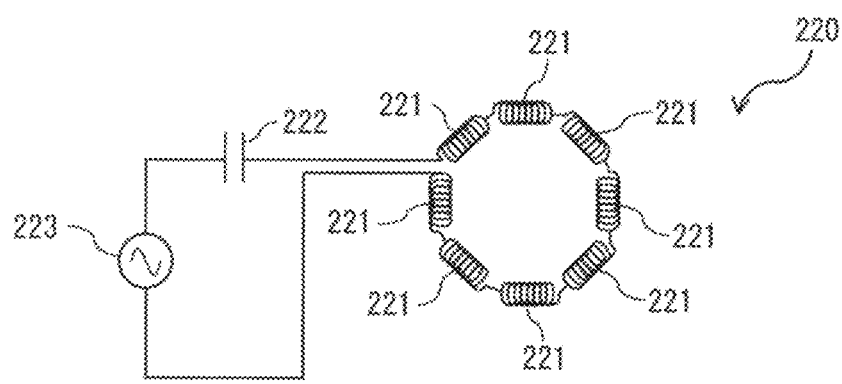
[FIG. 43A]
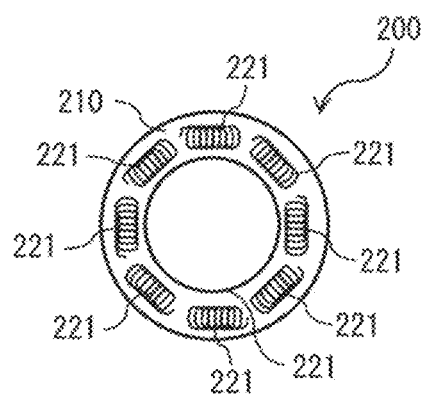

[ FIG. 43B ]
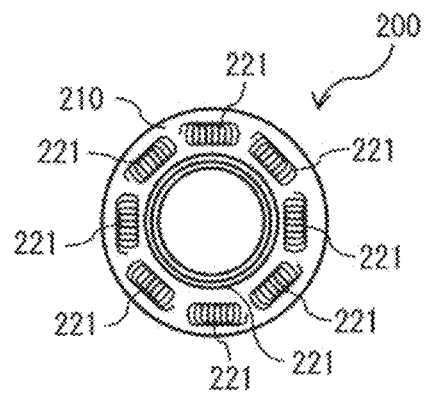
[ FIG. 44 ]
[ FIG. 45 ]
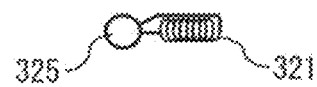
[ FIG. 46 ]
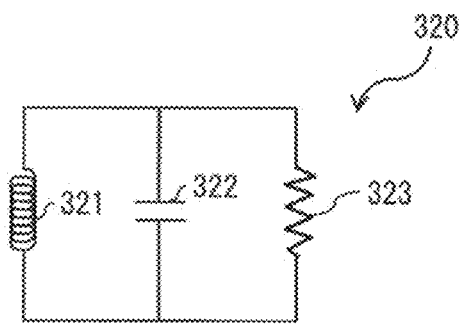

[ FIG. 47 ]
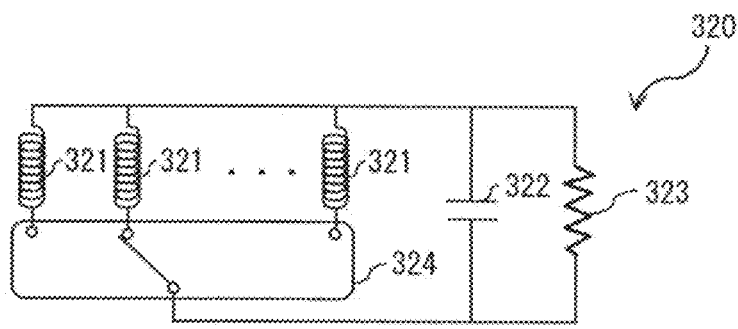
[ FIG. 48 ]
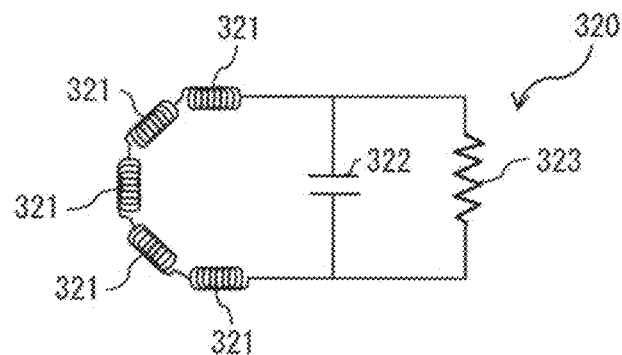
[ FIG. 49 ]
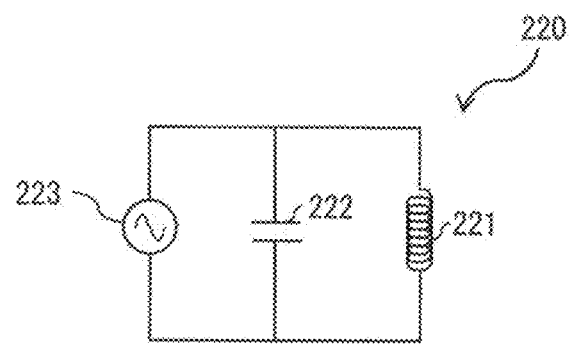
[ FIG. 50 ]
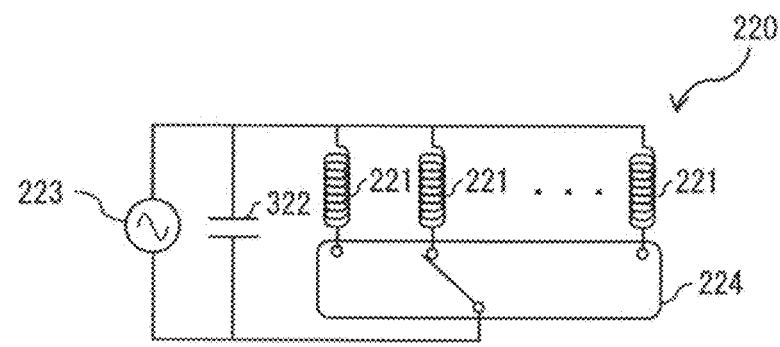

[ FIG. 51 ]
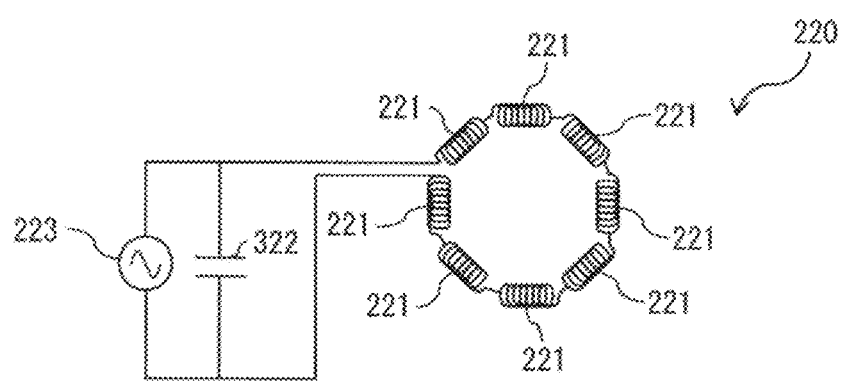

CONTACT LENS AND ACCESSORY

TECHNICAL FIELD

The present disclosure relates to a contact lens and an accessory.

BACKGROUND ART

In recent years, a method has been developed that acquires biological information using a contact lens.

CITATION LIST

Patent Literature

PTL 1: WO2014/181568

SUMMARY OF THE INVENTION

Incidentally, in a case where data is transmitted from a contact lens to peripheral equipment, wireless communication is typically utilized. In a case where the contact lens is worn on an eyeball, the contact lens gets wet with tears, which makes it non-straightforward to carry data sent out from the contact lens a long way. It is also considered to increase an output level of the data; however, such a case raises an issue with power consumption and an influence on a human body. Therefore, it is desirable to provide a contact lens and an accessory that allow for data transmission while suppressing the power consumption and the influence on a human body.

A contact lens according to an embodiment of the present disclosure includes: a lens section that is worn on an eyeball; an acquisition section that is provided in the lens section and acquires biological information; and an output section that outputs the biological information acquired by the acquisition section to an external apparatus to be worn on a human body. The output section has one or a plurality of coil antennas extending along a front surface of the lens section, and a capacitor that is coupled to the one or the plurality of coil antennas in series or in parallel.

In the contact lens according to the embodiment of the present disclosure, the biological information acquired by the acquisition section that is provided in the lens section is outputted to the external apparatus to be worn on a human body. This makes it possible to reduce an output level. Further, the capacitor is coupled to the one or the plurality of coil antennas in series or in parallel, which allows for wireless communication with use of magnetic coupling.

A first accessory according to an embodiment of the present disclosure includes a communication section that communicates with a contact lens. The communication section includes a plurality of coil antennas having different extending directions from one another, and a capacitor that is coupled to each of the coil antennas in series or in parallel.

In the first accessory according to the embodiment of the present disclosure, each of the coil antennas extends in a different direction from one another. This makes it easy to form a positional relationship that at least one coil antenna inside the first accessory is communicable with a coil antenna inside the contact lens, which allows the output level to be reduced. Further, the capacitor is coupled to each of the coil antennas in series or in parallel, allowing for the wireless communication with use of the magnetic coupling.

A second accessory according to an embodiment of the present disclosure includes a communication section that communicates with a contact lens. The communication section has a coil antenna extending in a direction that is communicable with the contact lens when the accessory is worn on a body, and a capacitor that is coupled to the coil antenna in series or in parallel.

In the second accessory according to the embodiment of the present disclosure, the coil antenna extends in a direction that is communicable with the contact lens when the second accessory is worn on a body. This makes it possible to reduce the output level. Further, the capacitor is coupled to the coil antenna in series or in parallel, allowing for the wireless communication with use of the magnetic coupling.

According to the contact lens, the first accessory, and the second accessory of the respective embodiments of the present disclosure, it is possible to establish the wireless communication with use of the magnetic coupling while reducing the output level, which allows for data transmission while reducing the power consumption and the influence on a human body. It is to be noted that effects of the present disclosure are not necessarily limitative to the effects described above, and any of effects described in the present specification may be provided.

BRIEF DESCRIPTION OF DRAWINGS

FIG. 1 is a diagram of an example of a schematic configuration of a biological information management system according to an embodiment of the present disclosure.

FIG. 2 is a diagram of an example of a configuration of a contact lens and an accessory illustrated in FIG. 1.

FIG. 3 is a diagram of an example of a communication section of the contact lens in FIG. 1 and a communication section of the accessory illustrated in FIG. 1.

FIG. 4 is a diagram of an example of the accessory illustrated in FIG. 1.

FIG. 5 is a diagram of an example of the accessory illustrated in FIG. 1.

FIG. 6 is a diagram of an example of the accessory illustrated in FIG. 1.

FIG. 7 is a diagram of an example of the accessory illustrated in FIG. 1.

FIG. 8 is a diagram of an example of the accessory illustrated in FIG. 1.

FIG. 9 is a diagram of an example of the accessory illustrated in FIG. 1.

FIG. 10 is a diagram of an example of the accessory illustrated in FIG. 1.

FIG. 11 is a diagram of an example of the accessory illustrated in FIG. 1.

FIG. 12 is a diagram of an example of the accessory illustrated in FIG. 1.

FIG. 13 is a diagram of an example of the accessory illustrated in FIG. 1.

FIG. 14 is a diagram of an example of the accessory illustrated in FIG. 1.

FIG. 15 is a diagram of an example of the accessory illustrated in FIG. 1.

FIG. 16A is a diagram of an example of a cross-sectional configuration of the contact lens illustrated in FIG. 1.

FIG. 16B is a diagram of an example of an exploded perspective configuration of a portion of the contact lens illustrated in FIG. 16A.

FIG. 17 is a diagram of an example of a functional block of the contact lens illustrated in FIG. 1.

FIG. 18 is a diagram of an example of a functional block of any of the accessories illustrated in FIG. 2 and FIG. 4 to FIG. 15.

FIG. 19 is a diagram of an example of a functional block of a terminal unit illustrated in FIG. 1.

FIG. 20 is a diagram of an example of a functional block of a data server unit illustrated in FIG. 1.

FIG. 21 is a diagram of an example of a functional block of a web server unit illustrated in FIG. 1.

FIG. 22 is a diagram of an example of transmission/reception steps of detection data in the biological information management system illustrated in FIG. 1.

FIG. 23 is a diagram of an example of transmission/reception steps of request data and analysis data in the biological information management system illustrated in FIG. 1.

FIG. 24(A) is a diagram of an example of a planer configuration of the contact lens illustrated in FIG. 1. (B) is a diagram of an example of a lateral configuration of the contact lens illustrated in FIG. 24(A).

FIG. 25A is a diagram of a modification example of the planer configuration of the contact lens illustrated in FIG. 1.

FIG. 25B is a diagram of an example of an exploded perspective configuration of a portion of the contact lens illustrated in FIG. 25 A.

FIG. 25C is a diagram of a modification example of the planer configuration of the contact lens illustrated in FIG. 1.

FIG. 26 is a diagram of a modification example of the accessory illustrated in FIG. 5.

FIG. 27 is a diagram of a modification example of the accessory illustrated in FIG. 2.

FIG. 28 is a diagram of a modification example of the accessory illustrated in FIG. 4.

FIG. 29 is a diagram of a modification example of the accessory illustrated in FIG. 5.

FIG. 30 is a diagram of a modification example of the accessory illustrated in FIG. 6.

FIG. 31 is a diagram of a modification example of the accessory illustrated in FIG. 7.

FIG. 32 is a diagram of a modification example of the accessory illustrated in FIG. 8.

FIG. 33 is a diagram of a modification example of the accessory illustrated in FIG. 1.

FIG. 34 is a diagram of a modification example of the accessory illustrated in FIG. 1.

FIG. 35 is a diagram of a modification example of the accessory illustrated in FIG. 1.

FIG. 36 is a diagram of a modification example of the accessory illustrated in FIG. 1.

FIG. 37 is a diagram of a modification example of the accessory illustrated in FIG. 1.

FIG. 38 is a diagram of an example of a circuit configuration of a communication section inside any of the accessories illustrated in FIG. 27 to FIG. 37.

FIG. 39 is a diagram of an example of a circuit configuration of the communication section inside any of the accessories illustrated in FIG. 27 to FIG. 37.

FIG. 40 is a diagram of a modification example of the planer configuration of the contact lens illustrated in FIG. 1.

FIG. 41 is a diagram of an example of a circuit configuration of a communication section inside the contact lens illustrated in FIG. 40.

FIG. 42 is a diagram of an example of a circuit configuration of the communication section inside the contact lens illustrated in FIG. 40.

FIG. 43A is a diagram of a modification example of the planer configuration of the contact lens illustrated in FIG. 1.

FIG. 43B is a diagram of a modification example of the planer configuration of the contact lens illustrated in FIG. 1.

FIG. 44 is a diagram of an example of a rotating mechanism that is provided in a communication section of the contact lens illustrated in FIG. 2.

FIG. 45 is a diagram of an example of a rotating mechanism that is provided in a communication section of the accessory illustrated in FIG. 2.

FIG. 46 is a diagram of a modification example of a circuit configuration of a communication section inside the accessory.

FIG. 47 is a diagram of a modification example of a circuit configuration of the communication section inside the accessory.

FIG. 48 is a diagram of a modification example of a circuit configuration of the communication section inside the accessory.

FIG. 49 is a diagram of a modification example of a circuit configuration of a communication section inside the contact lens.

FIG. 50 is a diagram of a modification example of a circuit configuration of the communication section inside the contact lens.

FIG. 51 is a diagram of a modification example of a circuit configuration of the communication section inside the contact lens.

MODES FOR CARRYING OUT THE INVENTION

Hereinafter, some embodiments of the present disclosure are described in detail with reference to the drawings. It is to be noted that descriptions are given in the following order.

1. Embodiment (FIG. 1 to FIG. 23)

An example where a coil antenna extending along a front surface of a lens is provided on a lens section 2. Modification Examples Modification Example A (FIG. 24)

An example where a coil antenna making substantially one round along a front surface of a lens is provided on a lens section Modification Example B (FIG. 25 and FIG. 26)

An example where a coil antenna extending in a direction perpendicular to a front surface of a lens is provided on a lens section Modification Example C (FIG. 27 to FIG. 39)

An example where a plurality of coil antennas is provided on an accessory

An example where a positional relationship between a coil antenna of an accessory and a coil antenna of a contact lens is determined uniquely (FIG. 27 to FIG. 32)

An example where a positional relationship between a coil antenna of an accessory and a coil antenna of a contact lens is not determined uniquely (FIG. 33 to FIG. 39)

Modification Example D (FIG. 40 to FIG. 42)

An example where a plurality of coil antennas is provided on a contact lens

Modification Example E (FIG. 43)

An example where a coil in FIG. 40 and a coil in FIG. 25A are provided on a contact lens Modification Example F (FIG. 44 and FIG. 45)

An example where a rotating mechanism is provided

Modification Example G (FIG. 46 to FIG. 51)

An example where a capacitor and a coil are coupled in parallel

1. Embodiment

[Configuration]

Description is provided on a biological information management system 1 according to an embodiment of the present disclosure. FIG. 1 illustrates a schematic configuration example of the biological information management system 1. The biological information management system 1 is a system that performs analysis in accordance with a request of a user on the basis of biological information of the user and outputs a result of the analysis to a mobile terminal (an external apparatus) owned by the user and the like.

The biological information management system 1 includes a contact lens 200, an accessory 300, a terminal unit 400, a data server unit 500, and a web server unit 600. The accessory 300, the terminal unit 400, the data server unit 500, and the web server unit 600 are coupled to one another over a network 100. The network 100 is, for example, a communication network that establishes communication using a communication protocol (TCP/IP) that is utilized normally in the Internet. The network 100 may be a secure communication network that establishes communication using, for example, its own original communication protocol. The network 100 is, for example, the Internet, an intranet, or a local area network. For example, the network 100 may be a wired LAN (Local Area Network), or may be a wireless LAN such as Wi-Fi, or a mobile phone line, and the like.

In contrast, the contact lens 200 performs near-field wireless communication (specifically, the wireless communication utilizing magnetic coupling) with the accessory 300. The communication between the contact lens 200 and the accessory 300 is performed in conformity with, for example, ISO/IEC 14443 (the international standard specification of a proximity-type RFID), ISO/IEC 18092 (the international standard of the wireless communication called NFC), or ISO/IEC 15693 (the international standard specification of the RFID), and the like.

(Contact Lens 200 and Accessory 300)

FIG. 2 illustrates an example of a configuration of the contact lens 200 and the accessory 300. Each of the contact lens 200 and the accessory 300 includes a communication section that performs the near-field wireless communication. Specifically, the contact lens 200 includes a communication section 220 that performs the near-field communication (specifically, the wireless communication utilizing the magnetic coupling), and the accessory 300 includes a communication section 320 that performs the near-field wireless communication (specifically, the wireless communication utilizing the magnetic coupling). The communication section 220 corresponds to a specific example of an "output section" in the present disclosure.

For example, as illustrated in FIG. 2 and FIG. 3, the communication section 220 includes a coil section 221, a capacitor 222, and an alternating-current source 223. The coil section 221 is a coil antenna extending along a front surface of a lens section 10. The coil antenna to be used for the coil section 221 is, for example, a solenoid type or a spiral type, and includes, for example, a metal such as gold or copper, a conductive polymer (for example, polyacetylene), carbon, or the like. The coil section 221 is disposed along an end edge of the lens section 10, for example. The capacitor 222 is coupled in series to the coil section 221. The alternating-current source 223 is coupled in series to the coil section 221 and the capacitor 222.

For example, as illustrated in FIG. 2 and FIG. 3, the communication section 320 includes a coil section 321, a capacitor 322, and a load 323. The coil section 321 is a coil antenna extending in a direction that is communicable with the communication section 220 of the contact lens 200 when the accessory 300 is worn on a body. The coil antenna to be used for the coil section 321 is, for example, the solenoid type or the spiral type, and includes, for example, a metal such as gold or copper, a conductive polymer (for example, polyacetylene), carbon, or the like. For example, when the accessory 300 is viewed from a front direction of the contact lens 200 with the accessory 300 worn on the body, the coil section 321 has a central axis parallel or substantially parallel to a central axis of the coil section 221. As a result, a common magnetic flux Φ passes through the coil section 221 and the coil section 321. The capacitor 322 is coupled in series to the coil section 221. The load 323 is, for example, a resistor of a predetermined value.

The accessory 300 takes a form that causes a positional relationship between the coil section 321 thereof and the coil section 221 of the contact lens 200 to be uniquely determined when the accessory 300 is worn on a body. Examples of the accessory 300 include an earphone, a necklace, eyeglasses, a tiepin, a badge, a headset, a cap or a hat, a helmet, a snorkeling mask, ski goggles, a hairpiece, or a wig.

In a case where the accessory 300 is an earphone 300a, the coil section 321 is built into a main body section 310a of the earphone 300a, as illustrated in FIG. 2, for example. In a case where the accessory 300 is a necklace 300b, the coil section 321 is provided on a neck-hanging section 310b of the necklace 300b, as illustrated in FIG. 4, for example. The necklace 300b is provided with precious metals or jewels to be hung at the breast, and such precious metals or jewels are sure to be disposed at the breast. Therefore, a position and an azimuth direction of the coil section 321 that is provided on the neck-hanging section 310b relative to the coil section 221 are also determined uniquely by necessity.

In a case where the accessory 300 is eyeglasses 300c, the coil section 321 is provided on a frame section 310c of the eyeglasses 300c, as illustrated in FIG. 5, for example. Since the eyeglasses 300c are provided with the frame section 310c to which lenses are fitted, and ear-hanging sections to be hooked behind ears, a position and an azimuth direction of the eyeglasses 300c relative to the coil section 221 are determined uniquely by necessity. As a result, a position and an azimuth direction of the coil section 321 that is provided on the eyeglasses 300c relative to the coil section 221 are also determined uniquely by necessity.

In a case where the accessory 300 is a tiepin 300d, the coil section 321 is provided on a main body section 310d of the tiepin 300d, as illustrated in FIG. 6, for example. Since the tiepin 300d is provided with a clasp that fixes a tie to a shirt behind the main body section 310d, a position and an azimuth direction of the tiepin 300d relative to the coil section 221 are determined uniquely by necessity. As a result, a position and an azimuth direction of the coil section 321 that is provided on the tiepin 300*d* relative to the coil section 221 are also determined uniquely by necessity.

In a case where the accessory 300 is a badge 300*e*, the coil section 321 is provided on a main body section 310*e* of the badge 300*e*, as illustrated in FIG. 7, for example. Since the badge 300*e* is provided with a clasp that fixes the badge 300*e* to clothing behind the main body section 310*e*, a position and an azimuth direction of the badge 300*e* are determined uniquely by necessity. As a result, a position and an azimuth direction of the coil section 321 that is provided on the badge 300*e* relative to the coil section 221 are also determined uniquely by necessity.

In a case where the accessory 300 is a headset 300*f*, the coil section 321 is provided on a main body section 310*f* of the headset 300*f*, as illustrated in FIG. 8, for example. Since the headset 300*f* is provided with a fastener (a band) that fixes the main body section 310*f* in front of eyes behind the main body section 310*f*, a position and an azimuth direction of the headset 300*f* relative to the coil section 221 are determined uniquely by necessity. As a result, a position and an azimuth direction of the coil section 321 that is provided on the headset 300*f* relative to the coil section 221 are also determined uniquely by necessity.

In a case where the accessory 300 is a cap 300*g*, the coil section 321 is provided on a visor 310*g*1, a crown 310*g*2, or the like of the cap 300*g*, as illustrated in FIG. 9, for example. Since the visor 310*g*1 is provided in a front part of the cap 300*g*, a position and an azimuth direction of the cap 300*g* relative to the coil section 221 are determined uniquely by necessity. As a result, a position and an azimuth direction of the coil section 321 that is provided on the cap 300*g* relative to the coil section 221 are also determined uniquely by necessity.

In a case where the accessory 300 is a hat 300*h*, the coil section 321 is provided on a brim 310*h*1, a crown 310*h*2, or the like of the hat 300*h*, as illustrated in FIG. 10, for example. Since the hat 300*h* is provided with a ribbon 310*h*3, a position and an azimuth direction of the hat 300*g* relative to the coil section 221 are determined uniquely by necessity. As a result, a position and an azimuth direction of the coil section 321 that is provided on the hat 300*h* relative to the coil section 221 are also determined uniquely by necessity.

In a case where the accessory 300 is a helmet 300*i*, the coil section 321 is provided at an end edge of an opening 310*i*, or the like of the helmet 300*i*, as illustrated in FIG. 11, for example. Since the opening 310*i* is provided in a front part of the helmet 300*i*, a position and an azimuth direction of the helmet 300*i* relative to the coil section 221 are determined uniquely by necessity. As a result, a position and an azimuth direction of the coil section 321 that is provided on the helmet 300*i* relative to the coil section 221 are also determined uniquely by necessity.

In a case where the accessory 300 is a mask 300*k* for snorkeling, the coil section 321 is provided on a lens section 310*k* or the like of the mask 300*k*, as illustrated in FIG. 12, for example. Since the mask 300*k* is provided with a fastener (a band) that fixes the lens section 310*k* in front of eyes, a position and an azimuth direction of the mask 300*k* relative to the coil section 221 are determined uniquely by necessity. As a result, a position and an azimuth direction of the coil section 321 that is provided on the mask 300*k* relative to the coil section 221 are also determined uniquely by necessity.

In a case where the accessory 300 is ski goggles 300*m*, the coil section 321 is provided on a lens section 310*m* or the like of the goggles 300*m*, as illustrated in FIG. 13, for example. Since the goggles 300*m* are provided with a fastener (a band) that fixes the lens section 310*m* in front of eyes, a position and an azimuth direction of the goggles 300*m* relative to the coil section 221 are determined uniquely by necessity. As a result, a position and an azimuth direction of the coil section 321 that is provided on the goggles 300*m* relative to the coil section 221 are also determined uniquely by necessity.

In a case where the accessory 300 is a hairpiece 300*n*, the coil section 321 is provided along a longitudinal direction of the hairpiece 300*n*, as illustrated in FIG. 14, for example. Therefore, a position and an azimuth direction of the hairpiece 300*n* relative to the coil section 221 are determined uniquely by necessity. As a result, a position and an azimuth direction of the coil section 321 that is provided on the hairpiece 300*n* relative to the coil section 221 are also determined uniquely by necessity.

In a case where the accessory 300 is a wig 300*p*, the coil section 321 is provided along a longitudinal direction of hair of the wig 300*p*, as illustrated in FIG. 15, for example. Therefore, a position and an azimuth direction of the wig 300*p* relative to the coil section 221 are determined uniquely by necessity. As a result, a position and an azimuth direction of the coil section 321 that is provided on the wig 300*p* relative to the coil section 221 are also determined uniquely by necessity.

FIG. 16A illustrates an example of a cross-sectional configuration of the contact lens 200. FIG. 16B illustrates an example of an exploded perspective configuration of a portion of the contact lens 200 in FIG. 16A. The contact lens 200 includes the coil section 221 and the capacitor 222 inside a lens section 210. For example, the lens section 210 has a substrate layer 211 on a front surface on the side of an eyeball, and further has a cover layer 212 on a front surface on the opposite side of the eyeball. Additionally, the lens section 210 has a layered body in which the coil section 221, the capacitor 222, and the like are provided, between the substrate layer 211 and the cover layer 212. The layered body has, for example, a structure that stacks, from the eyeball side, a functional layer 213, an intermediate layer 214, and a functional layer 215.

The substrate layer 211 includes, for example, light-transmissive resin, and serves as a supporting substrate that supports an optical element 20. The cover layer 212 includes, for example, light-transmissive resin, and serves to protect the communication section 220 and the like. The functional layer 213 includes a plurality of wiring layers 213A that configures a portion of the coil section 221, and a pad layer 213B that configures a portion of the capacitor 222. Each of the wiring layers 213A takes a rod-shaped form extending in a common direction, as illustrated in FIG. 16B, for example. The pad layer 213B is provided in the same layer as the wiring layer 213A. In the functional layer 213, a remaining part other than the wiring layer 213A and the pad layer 213B includes, for example, an insulating layer. The functional layer 215 includes a plurality of wiring layers 215A that configures a portion of the coil section 221, and a pad layer 215B that configures a portion of the capacitor 222. For example, as illustrated in FIG. 16B, each of the wiring layers 215A takes the rod-shaped form extending in a common direction, the direction being different from the direction in which each of the wiring layers 213A extends. Each of the wiring layers 215A is disposed in such a manner that the coil section 221 takes a spiral form having a rotating central axis in an in-plane direction. The pad layer 215B is provided in the same layer as the wiring layer 215A. In the functional layer 215, a remaining part other than the wiring layer 215A and the pad layer 215B includes, for example, an insulating layer. The intermediate layer 214 has a connecting section 214A that configures a portion of the coil section 221. The connecting section 214A couples electrically the wiring layer 213A and the wiring layer 215A to each other. In the intermediate layer 214, a remaining part other than the connecting section 214A includes, for example, an insulating layer. In other words, the connecting section 214A is provided in the same layer as the insulating layer inside the intermediate layer 214. The wiring layer 213A and the wiring layer 215A are disposed, for example, with the insulating layer inside the intermediate layer 214 sandwiched therebetween. A portion that is interposed between the wiring layer 213A and the wiring layer 215A in the insulating layer inside the intermediate layer 214 may include, for example, a magnetic material such as ferrite.

(Contact Lens 200)

FIG. 17 illustrates an example of a functional block of the contact lens 200. The contact lens 200 includes, for example, a storage section 230, a sensor section 240, the communication section 220, and a control section 250. The sensor section 240 corresponds to a specific example of an "acquisition section" in the present disclosure. The communication section 220 and the control section 250 correspond to a specific example of an "output section" in the present disclosure.

The storage section 230 includes, for example, a non-volatile memory, and includes, for example, an EEPROM (Electrically Erasable Programmable Read-Only Memory), a flash memory, a resistive random access memory, or the like. The storage section 230 stores a program (for example, a processing program 232) to be executed by the control section 250, and the like. The processing program 232 is a program serving to acquire detection data 231 corresponding to biological information from the sensor section 240, or to output the acquired detection data 231 to the accessory 300 through the communication section 220. The detection data 231 is data obtained using the contact lens 200, and is specifically the biological information detected by the sensor section 240. The control section 250 includes a processor, and executes, for example, the processing program 232 stored in the storage section 230. A function of the control section 250 is achieved in such a manner that the processing program 232 is executed by the control section 250, for example. The control section 250 and the communication section 22 output the biological information (the detection data 231) acquired by the sensor section 240 to the accessory 300 to be worn on a human body.

The sensor section 240 is provided in the lens section 210. The sensor section 240 acquires biological information of a user on whom the contact lens 200 is worn. The sensor section 240 is a device that detects, for example, specific ingredients contained in tears (for example, salt content, oxygen, lipid, blood glucose values, or hormonal substances). In such a case, the data (the detection data 231) to be obtained by being detected by the sensor section 240 is information concerning the ingredients of the tears. It is to be noted that the sensor section 240 may be, for example, a device that detects a line of sight, a device that detects states of blood vessels inside an eyeball, a device that detects pulses of blood vessels inside an eyeball, or a device that detects an eye pressure. In a case where the sensor section 240 is the device that detects the line of sight, the detection data 231 is biological information concerning the line of sight. In a case where the sensor section 240 is the device that detects the states of the blood vessels inside the eyeball, the detection data 231 is information concerning the blood vessels inside the eyeball. In a case where the sensor section 240 is the device that detects the eye pressure, the detection data 231 is biological information concerning the eye pressure. In a case where the sensor section 240 is a device that detects opening/closing of an eyelid, the detection data 231 is biological information concerning the opening/closing of the eyelid.

(Accessory 300)

FIG. 18 illustrates an example of a functional block of the accessory 300. The accessory 300 includes, for example, a storage section 340, communication sections 320 and 330, a functional section 350, and a control section 360.

The communication section 320 performs near-field wireless communication with the contact lens 200. Specifically, the communication section 320 acquires the detection data 231 corresponding to the biological information from the storage section 230 of the contact lens 200. The communication section 330 performs communication with the web server unit 600 over the network 100. Specifically, the communication section 330 outputs the detection data 231 acquired by the communication section 320 to the web server unit 600 over the network 100.

The storage section 340 includes, for example, a non-volatile memory, and includes, for example, an EEPROM, a flash memory, a resistive random access memory, or the like. The storage section 340 stores a program (for example, a processing program 341) to be executed by the control section 360, and the like. The processing program 341 is a program serving to acquire the detection data 231 from the contact lens 200 through the communication section 320, or to output the acquired detection data 231 to the web server unit 600 through the communication section 330 and over the network 100. The control section 360 includes a processor, and executes, for example, the processing program 341 stored in the storage section 340. A function of the control section 360 is achieved in such a manner that the processing program 341 is executed by the control section 360, for example.

(Terminal Unit 400)

FIG. 19 illustrates an example of a functional block of the terminal unit 400. The terminal unit 400 is a terminal apparatus to be used for a user to enter a request necessary for analysis of biological information, or for displaying an analysis result according to a request of a user. The terminal unit 400 has an interface serving to accept a request from a user, or to display an analysis result according to the request of a user. The terminal unit 400 includes, for example, a storage section 410, a communication section 420, an acceptance section 430, a display section 440, and a control section 450.

The acceptance section 430 includes a keyboard, a touch panel, and the like. The display section 440 performs display based on an image signal inputted from the control section 450. In a case where the display section 440 has a function of the touch panel, the function of the touch panel may take charge of a function of the acceptance section 430. The storage section 410 stores programs (for example, a web browser program 413 and an operating system) to be executed by the control section 450, and the like. The storage section 410 stores request data 411 and analysis data 412.

The request data 411 is data concerning a request accepted from a user. The request from the user includes, for example, a request for a performance or conditioning management based on biological information of the user. The analysis data 412 is data concerning an analysis result responding to the request data 411. The analysis data 412 is data concerning the performance or conditioning of the user.

The control section 450 includes a processor, and executes the web browser program 413 stored in the storage section 410, the operating system, and the like. A user interface (the display section 440) in the terminal unit 400 is achieved by processing, for example, an application (for example, html data) acquired from the web server unit 600 using the web browser program 413.

(Data Server Unit 500)

FIG. 20 illustrates an example of a functional block of the data server unit 500. The data server unit 500 is an apparatus that serves to store, for example, the detection data 231 obtained using the contact lens 200, and analysis data 611 obtained from data processing in the web server unit 600.

The data server unit 500 includes, for example, a storage section 510, a communication section 520, and a control section 530. The control section 530 causes information inputted from an outside through the communication section 520 to be stored in the storage section 510, or causes readout information from the storage section 510 to be outputted to the outside through the communication section 520. The communication section 520 performs communication with other apparatuses over the network 100. The storage section 510 includes, for example, a non-volatile memory, and includes, for example, an EEPROM, a flash memory, a resistive random access memory, or the like. The storage section 510 stores the detection data 231 and the analysis data 611.

(Web Server Unit 600)

FIG. 21 illustrates an example of a functional block of the web server unit 600. The web server unit 600 provides the user interface in the terminal unit 400. The web server unit 600 further generates an analysis result (the analysis data 611) responding to the request data 411 accepted from a user on the basis of the analysis data 611 obtained using the contact lens 200. The web server unit 600 includes, for example, a storage section 610, a communication section 620, and a control section 630.

The communication section 620 performs communication with the other units (for example, the data server unit 500, the terminal unit 400, and the like) in the biological information management system 1 over the network 100. The storage section 610 includes, for example, a non-volatile memory, and includes, for example, an EEPROM, a flash memory, a resistive random access memory, or the like. The storage section 610 stores programs (for example, a web server program 612 and a web application program 613) to be executed by the control section 630, and the like. The web application program 613 is an application program to be used over the network 100. The web application program 613 is a program that generates the analysis result (the analysis data 611) responding to the request data 411 accepted from a user on the basis of the analysis data 611 obtained using the contact lens 200. The web application program 613 operates in collaboration between the web server program 612 and the web browser program 413.

The control section 630 includes a processor, and executes, for example, the web server program 612 and the web application program 613 that are stored in the storage section 610, and the like. A function of the control section 630 is achieved, for example, in such a manner that the web server program 612 and the web application program 613 are executed by the control section 630. Specifically, the control section 630 generates the analysis result (the analysis data 611) responding to the request data 411 accepted from a user on the basis of the analysis data 611 obtained using the contact lens 200.

When the detection data 231 satisfies a predetermined condition, the control section 630 may generate a control signal 630A for notifying such a state, and outputs the generated control signal 630A to the terminal unit 400 through the communication section 520. The "predetermined condition" refers to, for example, a condition calling for drawing attention in performance or conditioning of a user. The control signal 630A is, for example, text data for drawing attention.

[Operation]

(Storage of Detection Data)

Next, description is provided on steps of storing the detection data 231 in the biological information management system 1.

FIG. 22 illustrates an example of transmission/reception steps of the detection data 231 in the biological information management system 1. Initially, a user wears the contact lens 200 on his/her own eyeball. Thereafter, in the contact lens 200, the sensor section 240 acquires biological information (the detection data 231) of the user (Step S101). In a case where the sensor section 240 is a device that detects specific ingredients contained in tears (for example, salt content, oxygen, lipid, or blood glucose values), the detection data 231 is biological information concerning the tears. In a case where the sensor section 240 is a device that detects a line of sight, the detection data 231 is biological information concerning the line of sight. In a case where the sensor section 240 is a device that detects states of blood vessels inside an eyeball, the detection data 231 is biological information concerning the eyeball. In a case where the sensor section 240 is a device that detects an eye pressure, the detection data 231 is biological information concerning the eyeball.

The sensor section 240 transmits the acquired biological information (the detection data 231) to the accessory 300 through the communication section 220 (Step S102). On receiving the detection data 231 from the sensor section 240 (Step S103), the accessory 300 transmits the received detection data 231 to the data server unit 500 (Step S104). On receiving the detection data 231 from the accessory 300 (Step S105), the data server unit 500 stores the received detection data 231 in the storage section 510 (Step S106).

(Analysis of Detection Data)

Next, description is provided on analysis steps of the detection data 231 in the biological information management system 1.

FIG. 23 illustrates an example of the analysis steps of the detection data 231 in the biological information management system 1. Initially, a user requests for the terminal unit 400 to display a user interface for entering a request. In response to this, the terminal unit 400 displays the user interface for entering the request on the display section 440 by processing an application acquired from the web server unit 600 using the web browser program 413. The user enters the request data 411 using the displayed user interface and the acceptance section 430. On accepting the request data 411 entered from the user (Step S201), the terminal unit 400 transmits the accepted request data 411 to the web server unit 600 (Step S202).

On receiving the request data 411 from the terminal unit 400 (Step S203), the web server unit 600 reads out the detection data 231 corresponding to contents of the received request data 411 from the data server unit 500 (Step S204). The web server unit 600 generates an analysis result (the analysis data 611) responding to the request data 411 on the basis of the readout detection data 231 (Step S205). The web server unit 600 transmits the generated analysis data 611 to the terminal unit 400 (Step S206). On receiving the analysis data 611 from the web server unit 600 (Step S207), the terminal unit 400 displays the received analysis data 611 on the display section 440 (Step S208).

Effects

Next, description is provided on effects of the biological information management system 1 according to the present embodiment.

In the present embodiment, the biological information (the detection data 231) acquired by the sensor section 240 that is provided in the lens section 10 is outputted to the accessory 300 worn on a human body. This allows an output level to be reduced. Further, the capacitor 222 is coupled to the coil section 221 in series, which allows for the wireless communication utilizing the magnetic coupling. As a result, it is possible to transmit data while suppressing the power consumption and the influence on a human body.

Further, in the present embodiment, in a case where the coil section 221 is disposed along an end edge of the lens section 210, there is no possibility that a view of a user will be blocked out by the coil section 221. This makes it possible to perform data transmission between the contact lens 200 and the accessory 300 in a state where a user wears the contact lens 200.

Additionally, in the present embodiment, in a case where the coil section 221 includes the two wiring layers 213A and 215A, and the connecting section 214A that are provided inside the lens section 210, it is possible to manufacture the coil section 221 using an IC (Integrated Circuit) process. This allows the coil section 221 to be fabricated in a smaller thickness and size, which makes it possible to perform data transmission without impairing feeling of wearing the contact lens 200.

Further, in the present embodiment, in a case where the capacitor 222 includes the two pad layers 213B and 215B that are provided inside the lens section 210, it is possible to manufacture the capacitor 222 using the IC process. This allows the capacitor 222 to be fabricated in a smaller thickness and size, which makes it possible to perform data transmission without impairing the feeling of wearing the contact lens 200.

In addition, in the present embodiment, the coil section 321 of the accessory 300 extends in a direction that is communicable with the coil section 221 of the contact lens 200 when the accessory 300 is worn on a body. This allows the output level to be reduced. Further, the capacitor 322 is coupled to the coil section 321 in series, which allows for the wireless communication utilizing the magnetic coupling. As a result, it is possible to transmit data while suppressing the power consumption and the influence on a human body.

Moreover, in the present embodiment, the accessory 300 takes the form that causes the positional relationship between the coil section 321 thereof and the coil section 221 of the contact lens 200 to be determined uniquely when the accessory 300 is worn on a body. This facilitates communication between the coil section 321 of the accessory 300 and the coil section 221 of the contact lens 200, which allows the output level to be reduced. As a result, it is possible to transmit data while suppressing the power consumption and the influence on a human body.

2. Modification Examples

Next, description is provided on modification examples of the contact lens 200 and the accessory 300 according to the above-described embodiment.

Modification Example A

FIG. 24(A) illustrates an example of a planar configuration of a contact lens 200 according to a modification example A. FIG. 24(B) illustrates an example of a lateral configuration of the contact lens 200 according to the modification example A. In the present modification example, the coil section 221 takes a substantially circular form extending along an end edge of the lens section 210. In the coil section 221, an opening at one end and an opening at another end are directed in opposite directions.

Further, in the coil section 221, the opening at the one end and the opening at the other end are provided inside layers that are different from each other. Even in a case where the coil section 221 adopts such a configuration, it is possible to reduce the output level, and to achieve the wireless communication utilizing the magnetic coupling. As a result, it is possible to transmit data while suppressing the power consumption and the influence on a human body.

Modification Example B

FIG. 25A illustrates an example of a planer configuration of a contact lens 200 according to a modification example B. FIG. 25B illustrates an example of an exploded perspective configuration of a portion of the contact lens 200 illustrated in FIG. 25A. In the present modification example, the coil section 221 extends in a direction perpendicular to a front surface of the lens section 210. At this time, the coil section 221 takes a substantially circular form extending along an end edge of the lens section 210, for example. The coil section 221 includes, for example, a wiring line of a spiral form having a rotating central axis in a direction intersecting with the front surface of the lens section 210. For example, the lens section 210 has the substrate layer 211 on a front surface on the side of an eyeball, and further has the cover layer 212 on a front surface on the opposite side of the eyeball. Additionally, the lens section 210 has the layered body in which the coil section 221, the capacitor 222, and the like are provided, between the substrate layer 211 and the cover layer 212. The layered body has, for example, a structure that stacks the functional layer 213, the intermediate layer 214, the functional layer 215, an intermediate layer 216, and a functional layer 217 from the eyeball side.

The functional layer 213 includes a wiring layer 213C that configures a portion of the coil section 221, and the pad layer 213B that configures a portion of the capacitor 222. For example, as illustrated in FIG. 25B, the wiring layer 213C takes a C-shaped form. The pad layer 213B is provided in the same layer as the wiring layer 213C. In the functional layer 213, a remaining part other than the wiring layer 213C and the pad layer 213B includes, for example, an insulating layer. The functional layer 215 has a wiring layer 215C that configures a portion of the coil section 221. For example, as illustrated in FIG. 25B, the wiring layer 215C takes the C-shaped form. The wiring layer 215C is disposed in such a manner that the coil section 221 takes a spiral form having a rotating central axis in a stacking direction. The pad layer 215B is provided in the same layer as the wiring layer 215C. In the functional layer 215, a remaining part other than the wiring layer 215C and the pad layer 215B includes, for example, an insulating layer. The functional layer 217 has a wiring layer 217C that configures a portion of the coil section 221. For example, as illustrated in FIG. 25B, the wiring layer 217C takes the C-shaped form. The wiring layer 217C is disposed in such a manner that the coil section 221 takes the spiral form having the rotating central axis in the stacking direction. A pad layer 217B is provided in the same layer as the wiring layer 215C. In the functional layer 217, a remaining part other than the wiring layer 217C and the pad layer 217B includes, for example, an insulating layer.

The intermediate layer 214 has the connecting section 214A that configures a portion of the coil section 221. The connecting section 214A couples electrically the wiring layer 213C and the wiring layer 215C to each other. In the intermediate layer 214, a remaining part other than the connecting section 214A includes, for example, an insulating layer. In other words, the connecting section 214A is provided in the same layer as the insulating layer inside the intermediate layer 214. The wiring layer 213C and the wiring layer 215C are disposed, for example, with the insulating layer inside the intermediate layer 214 sandwiched therebetween. A portion that is interposed between the wiring layer 213C and the wiring layer 215C in the insulating layer inside the intermediate layer 214 may include, for example, a magnetic material such as ferrite. The intermediate layer 216 has a connecting section 216A that configures a portion of the coil section 221. The connecting section 216A couples electrically the wiring layer 215C and the wiring layer 217C to each other. In the intermediate layer 216, a remaining part other than the connecting section 216A includes, for example, an insulating layer. In other words, the connecting section 216A is provided in the same layer as the insulating layer inside the intermediate layer 214. The wiring layer 215C and the wiring layer 217C are disposed, for example, with the insulating layer inside the intermediate layer 216 sandwiched therebetween. A portion that is interposed between the wiring layer 215C and the wiring layer 217C in the insulating layer inside the intermediate layer 216 may include, for example, the magnetic material such as the ferrite.

It is to be noted that, in the present modification example, the coil section 221 may include a wiring line of a spiral form having a rotating central axis in a direction extending toward a direction intersecting with the front surface of the lens section 210, as illustrated in FIG. 25C, for example. In such a case, the coil section 221 may become a wiring line of a spiral form having the rotating central axis in the direction intersecting with the front surface of the lens section 210, or may become a wiring line wound spirally in a plane parallel to the front surface of the lens section 210.

Here, for example, when the accessory 300 is viewed from a front direction of the contact lens 200 with the accessory 300 worn on a body, the coil section 321 of the accessory 300 has a central axis parallel or substantially parallel to a central axis of the coil section 221. As a result, a common magnetic flux $\Phi$ passes through the coil section 221 and the coil section 321.

In a case where the accessory 300 is the eyeglasses 300c as illustrated in FIG. 26, for example, the coil section 321 is formed, for example, in such a manner that a central axis of the coil section 321 is shared with the central axis of the coil section 221. In a case where the accessory 300 is the eyeglasses 300c as illustrated in FIG. 26, for example, the coil section 321 is formed along the frame section 310c, for example. Even in a case where the coil sections 221 and 321 are each structured in such a configuration, it is possible to reduce the output level, and to achieve the wireless communication utilizing the magnetic coupling. As a result, it is possible to transmit data while suppressing the power consumption and the influence on a human body.

Modification Example C

Each of FIG. 27 to FIG. 32 illustrates a modification example of the accessory 300. Each of the accessories 300 illustrated in FIG. 27 to FIG. 32 has multiple coil sections 321 that are different in extending directions from one another.

Each of the accessories 300 illustrated in FIG. 27 to FIG. 32 takes the form that causes a positional relationship between each of the coil sections 321 thereof and the coil section 221 of the contact lens 200 to be uniquely determined when the relevant accessory 300 is worn on a body.

FIG. 27 exemplifies how the multiple coil sections 321 that are different in the extending directions from one another are provided in the earphone 300a illustrated in FIG. 2. FIG. 28 exemplifies how the multiple coil sections 321 that are different in the extending directions from one another are provided in the necklace 300b illustrated in FIG. 4. FIG. 29 exemplifies how the multiple coil sections 321 that are different in the extending directions from one another are provided in the eyeglasses 300c illustrated in FIG. 5. FIG. 30 exemplifies how the multiple coil sections 321 that are different in the extending directions from one another are provided in the tiepin 300d illustrated in FIG. 6. FIG. 31 exemplifies how the multiple coil sections 321 that are different in the extending directions from one another are provided in the badge 300e illustrated in FIG. 7. FIG. 32 exemplifies how the multiple coil sections 321 that are different in the extending directions from one another are provided in the headset 300f illustrated in FIG. 8.

In each of the accessories 300 illustrated in FIG. 27 to FIG. 32, the positional relationship between each of the coil sections 321 thereof and the coil section 221 of the contact lens 200 is determined uniquely when the relevant accessory 300 is worn on a body. This facilitates communication between the at least one coil section 321 in the accessory 300 and the coil section 221 of the contact lens 200, which allows the output level to be reduced. As a result, it is possible to transmit data while suppressing the power consumption and the influence on a human body. It is to be noted that, in a case where the multiple coil sections 321 that are different in the extending directions from one another are provided in each of the accessories 300 illustrated in FIG. 9 to FIG. 15, each of the relevant accessories 300 takes the form that causes the positional relationship between each of the coil sections 321 thereof and the coil section 221 of the contact lens 200 to be uniquely determined when the relevant accessory 300 is worn on a body, as with the accessories 300 illustrated in FIG. 27 to FIG. 32. Therefore, also in a case where the multiple coil sections 321 that are different in the extending directions from one another are provided in each of the accessories 300 illustrated in FIG. 9 to FIG. 15, the communication between the at least one coil section 321 in the accessory 300 and the coil section 221 of the contact lens 200 is facilitated, which allows the output level to be reduced. As a result, it is possible to transmit data while suppressing the power consumption and the influence on a human body.

Each of the accessories 300 illustrated in FIG. 33 to FIG. 37 takes the form that does not cause the positional relationship between each of the coil sections 321 thereof and the coil section 221 of the contact lens 200 to be determined uniquely when the relevant accessory 300 is worn on a body, or is intended to be worn on an arm, an finger, or a leg. Examples of the accessories 300 illustrated in FIG. 33 to FIG. 37 include a necklace 300$q$, a bracelet 300$r$, an earring 300$s$, a finger ring 300$t$, or a wristwatch 300$u$.

FIG. 33 exemplifies the necklace 300$q$ for which a position of breast is not specifically identified as the accessory 300. In the necklace 300$q$, a whole part thereof serves as a neck-hanging section, and, for example, precious metals, jewels, or the like are disposed in line on the neck-hanging section. In the necklace 300$q$, the multiple coil sections 321 are disposed side by side at even intervals along the neck-hanging section, for example. Each time the necklace 300$q$ is worn on a body, a position and an azimuth direction of the specific coil section 221 in the necklace 300$q$ relative to the coil section 221 of the contact lens 200 are typically different. Therefore, the positional relationship between each of the coil sections 321 and the coil section 221 of the contact lens 200 is not determined uniquely.

FIG. 34 exemplifies the bracelet 300$r$ without any distinction of upper and lower parts thereof as the accessory 300. The bracelet 300$r$ is in the ring form in which, for example, precious metals, jewels, or the like are disposed in line. In the bracelet 300$r$, the multiple coil sections 321 are disposed side by side at even intervals along the precious metals, the jewels, or the like, for example. Each time the bracelet 300$r$ is worn on a body, a position and an azimuth direction of the specific coil section 221 in the bracelet 300$r$ relative to the coil section 221 of the contact lens 200 are typically different. Therefore, the positional relationship between each of the coil sections 321 and the coil section 221 of the contact lens 200 is not determined uniquely.

FIG. 35 exemplifies the earring 300$s$ as the accessory 300. The earring 300$s$ has an ear-hanging section 310$s$ that is fixed on an ear, and a ring section 310$t$ that is fixed to the ear-hanging section 310$s$ in a swingable manner. The ring section 310$t$ is in the ring form that includes, for example, precious metals. In the earring 300$s$, the multiple coil sections 321 are disposed side by side at even intervals on the ring section 310$t$, for example. When the earring 300$s$ is worn on a body, the ring section 310$t$ in the earring 300$s$ is swinging in response to motion of a person. Therefore, the positional relationship between each of the coil sections 321 and the coil section 221 of the contact lens 200 is not determined uniquely.

FIG. 36 exemplifies the finger ring 300$t$ as the accessory 300. The finger ring 300$t$ includes a ring section 310$u$ having an opening size allowing for insertion into a predetermined finger. In the ring section 310$u$, the multiple coil sections 321 are disposed side by side at even intervals on the ring section 310$u$, for example. Since the finger is moved actively in daily life, the positional relationship between each of the coil sections 321 of the finger ring 300$t$ slipped on the finger and the coil section 221 of the contact lens 200 is not determined uniquely.

FIG. 37 exemplifies the wristwatch 300$u$ as the accessory 300. The wristwatch 300$u$ includes a main body section 310$v$ that displays the time and the like, and a belt section 310$w$ that serves to fix the main body section 310$v$ to an arm. In the belt section 310$w$, the multiple coil sections 321 are disposed to cause the respective coil sections 321 to have different extending directions from one another in the belt section 310$w$, for example. Since the arm is moved actively in daily life, the positional relationship between each of the coil sections 321 of the wristwatch 300$u$ worn on the arm and the coil section 221 of the contact lens 200 is not determined uniquely.

As described above, in each of the accessories 300 illustrated in FIG. 33 to FIG. 37, the positional relationship between each of the coil sections 321 thereof and the coil section 221 of the contact lens 200 is not determined uniquely when the relevant accessory 300 is worn on a body. However, the respective coil sections 321 are different in the extending directions from one another. This facilitates communication between the at least one coil section 321 in the accessory 300 and the coil section 221 of the contact lens 200, which allows the output level to be reduced. As a result, it is possible to transmit data while suppressing the power consumption and the influence on a human body.

FIG. 38 illustrates an example of a circuit configuration of the communication section 320 that is provided in each of the accessories 300 described in FIG. 27 to FIG. 37. In the present modification example, for example, as illustrated in FIG. 38, the communication section 320 includes the multiple coil sections 321 that are different in the extending directions from one another, the capacitor 322 and the load 323 that are coupled in series to each of the coil sections 321, and a multiplexer 324. One ends of the respective coil sections 321 are coupled electrically with one another. The capacitor 322 and the load 323 are coupled in series to each of the coil sections 321 through a connecting point where the one ends of the respective coil sections 321 are coupled electrically with one another. The multiplexer 324 is a switch that electrically couples the one coil section 321 selected from among the multiple coil sections 321 and the load 323 with each other.

The one coil section 321 contributing to communication with the coil section 221 is selected by the multiplexer 324 from among the multiple coil sections 321, which makes it possible to achieve extremely low power consumption. This allows for data transmission while suppressing the power consumption and the influence on a human body.

It is to be noted that, in the present modification example, for example, as illustrated in FIG. 39, the coil sections 321 may be coupled in series with one another. In such a case, the multiplexer 324 is unnecessary, and the multiple coil sections 321 coupled in series with one another are coupled in series to the capacitor 322 and the load 323. Even in such a case, a distance between each of the coil sections 321 and the coil section 221 is comparatively small, which makes it possible to transmit data while suppressing the power consumption and the influence on a human body.

Modification Example D

FIG. 40 illustrates a modification example of a planar configuration of the contact lens 200. In the present modification example, the contact lens 200 has the multiple coil sections 221 extending along a front surface of the lens section 210. The multiple coil sections 221 are disposed, for example, along an end edge of the lens section 210.

FIG. 41 illustrates an example of a circuit configuration of the communication section 220 that is provided in the contact lens 200 according to the present modification example. In the present modification example, for example, as illustrated in FIG. 41, the communication section 220 includes the multiple coil sections 221 that are different in the extending directions from one another, the capacitor 222 and the alternating-current source 223 that are coupled in series to each of the coil sections 221, and a multiplexer 224. One ends of the respective coil sections 221 are coupled electrically with one another. The capacitor 222 and the alternating-current source 223 are coupled in series to each of the coil sections 221 through a connecting point where the one ends of the respective coil sections 221 are coupled electrically with one another. The multiplexer 224 is a switch that electrically couples the one coil section 221 selected from among the multiple coil sections 221 and the alternating-current source 223 with each other.

The one coil section 221 contributing to communication with the coil section 321 is selected by the multiplexer 224 from among the multiple coil sections 221, which makes it possible to achieve extremely low power consumption. This allows for data transmission while suppressing the power consumption and the influence on a human body.

It is to be noted that, in the present modification example, for example, as illustrated in FIG. 42, the coil sections 221 may be coupled in series with one another. In such a case, the multiplexer 224 is unnecessary, and the multiple coil sections 221 coupled in series with one another are coupled in series to the capacitor 222 and the alternating-current source 223. Even in such a case, a distance between each of the coil sections 221 and the coil section 321 is comparatively small, which makes it possible to transmit data while suppressing the power consumption and the influence on a human body.

Modification Example E

FIG. 43A illustrates a modification example of a planar configuration of the contact lens 200. In the present modification example, the contact lens 200 has the multiple coil sections 221 extending along a front surface of the lens section 210, and the one or multiple coil sections 221 extending in a direction intersecting with the front surface of the lens section 210. The one or multiple coil sections 221 extending in the direction intersecting with the front surface of the lens section 210 is provided, for example, in a region surrounded by the multiple coil sections 221 extending along the front surface of the lens section 210.

The one or multiple coil sections 221 extending in the direction intersecting with the front surface of the lens section 210 includes, for example, a wiring line of a spiral form having a rotating central axis in the direction intersecting with the front surface of the lens section 210. It is to be noted that, in FIG. 43A, the one coil section 221 extending in the direction intersecting with the front surface of the lens section 210 appears to include a single-winding wiring line. However, one reason why the one coil section 221 extending in the direction intersecting with the front surface of the lens section 210 looks like the single-winding wiring line is that the C-shaped wiring layers 215C as illustrated in FIG. 25B, for example, lay on top of each other in a stacking direction.

It is to be noted that, for example, as illustrated in FIG. 43B, the one or multiple coil sections 221 extending in the direction intersecting with the front surface of the lens section 210 may include a wiring line that is formed in a spiral shape in one plane parallel to the front surface of the lens section 210.

In the present modification example, the coil sections 221 may be coupled in series with one another. Further, in the present modification example, the one coil section 221 contributing to the communication with the coil section 321 may be selected by the multiplexer 224 from among the multiple coil sections 221.

As with the above-described embodiment and modification examples thereof, the present modification example allows for data transmission while suppressing the power consumption and the influence on a human body.

Modification Example F

In the above-described embodiment and modification examples thereof, for example, as illustrated in FIG. 44, the communication section 220 of the contact lens 200 may have a rotating mechanism 225. The rotating mechanism 225 is a mechanism that rotates the coil section 221 around the rotating mechanism 225, the rotating mechanism 225 serving as a center of rotation, and rotates the coil section 221 under manual or electrical control. Further, in the above-described embodiment and modification examples thereof, for example, as illustrated in FIG. 45, the communication section 320 of the accessory 300 may have a rotating mechanism 325. The rotating mechanism 325 is a mechanism that rotates the coil section 321 around the rotating mechanism 325, the rotating mechanism 325 serving as the center of rotation, and rotates the coil section 321 under the manual or electrical control.

Modification Example G

In the above-described embodiment and modification examples thereof, the capacitor 322 is coupled in series to the coil section 321, and the capacitor 222 is coupled in series to the coil section 221.

However, in the above-described embodiment and modification examples thereof, for example, as illustrated in FIG. 46, FIG. 47, and FIG. 48, the capacitor 322 may be coupled in parallel to the coil section 321. It is to be noted that FIG. 47 exemplifies how the capacitor 322 is coupled in parallel to each of the coil sections 321 and the multiplexer 324. Further, FIG. 48 exemplifies how the capacitor 322 is coupled in parallel to a current path including all of the coil sections 321 coupled in series.

Further, in the above-described embodiment and modification examples thereof, for example, as illustrated in FIG. 49, FIG. 50, and FIG. 51, the capacitor 222 may be coupled in parallel to the coil section 221. It is to be noted that FIG. 50 exemplifies how the capacitor 222 is coupled in parallel to each of the coil sections 221 and the multiplexer 224. Further, FIG. 51 exemplifies how the capacitor 222 is coupled in parallel to a current path including all of the coil sections 221 coupled in series.

As described above, even in a case where the capacitor 322 is coupled in series to the coil section 321, or the capacitor 222 is coupled in series to the coil section 221, it is possible to achieve data transmission while suppressing the power consumption and the influence on a human body, as with the above-described embodiment and modification examples thereof.

Modification Example H

In the above-described embodiment and modification examples thereof, the communication between the contact lens 200 (the communication section 220) and the accessory 300 (the communication section 320) may further use medium-distance wireless communication, such as WLAN (Wireless LAN), BT (Bluetooth®), and LTE (Long Term Evolution) in addition to the above-described near-field wireless communication. In such a case, it is possible to surely establish the communication between the contact lens 200 (the communication section 220) and the accessory 300 (the communication section 320).

The present disclosure is described thus far with reference to the embodiment and modification examples thereof; however, the present disclosure is not limited to the above-described embodiments and the like, but various modifications may be made. It is to be noted that the effects described in the present specification are merely exemplified. The effects of the present disclosure are not limited to the effects described herein. The present disclosure may have any effects other than the effects described herein.

Further, for example, the present disclosure may be configured as follows.

(1)

A contact lens including:
a lens section that is worn on an eyeball;
an acquisition section that is provided in the lens section and acquires biological information; and
an output section that outputs the biological information acquired by the acquisition section to an external apparatus to be worn on a human body, in which
the output section has one or a plurality of coil antennas extending along a front surface of the lens section, and a capacitor that is coupled to the one or the plurality of coil antennas in series or in parallel.

(2)

The contact lens according to (1), in which the one or the plurality of coil antennas is disposed along an end edge of the lens section.

(3)

The contact lens according to (1) or (2), in which the one or the plurality of coil antennas includes:
two wiring layers that are disposed with an insulating layer sandwiched therebetween; and
a connecting section that is provided inside a same layer as the insulating layer and electrically couples the two wiring layers to each other.

(4)

The contact lens according to (3), in which the capacitor includes two pad layers that are respectively provided inside same layers as the two wiring layers.

(5)

An accessory including a communication section that communicates with a contact lens,
in which the communication section includes a plurality of coil antennas having different extending directions from one another, and a capacitor that is coupled to each of the coil antennas in series or in parallel.

(6)

The accessory according to (5), in which the accessory takes a form that does not cause a positional relationship between each of the coil antennas and the contact lens is to be determined uniquely when the relevant accessory is worn on a body, or is to be worn on an arm, a finger, or a leg.

(7)

The accessory according to (6), in which the accessory is a necklace, a bracelet, an earring, a finger ring, or a wristwatch.

(8)

An accessory including a communication section that communicates with a contact lens,
in which the communication section includes a coil antenna extending in a direction that is communicable with the contact lens when the accessory is worn on a body, and a capacitor that is coupled to the coil antenna in series or in parallel.

(9)

The accessory according to (8), in which the relevant accessory takes a form that causes a positional relationship between the coil antenna and the contact lens to be determined uniquely when the accessory is worn on a body.

(10)

The accessory according to (9), in which the accessory is an earphone, a necklace, eyeglasses, a tiepin, a badge, a headset, a cap or a hat, a helmet, a snorkeling mask, ski goggles, a hairpiece, or a wig.

This application claims the priority on the basis of Japanese Patent Application No. 2017-195326 filed on Oct. 5, 2017 with Japan Patent Office, the entire contents of which are incorporated in this application by reference.

It should be understood by those skilled in the art that various modifications, combinations, sub-combinations, and alterations may occur depending on design requirements and other factors insofar as they are within the scope of the appended claims or the equivalents thereof.

The invention claimed is:

1. A contact lens comprising:
a lens section that is worn on an eyeball;
an acquisition section that is provided in the lens section and acquires biological information; and
an output section that outputs the biological information acquired by the acquisition section to an external apparatus, wherein
the output section has one or a plurality of coil antennas extending along a front surface of the lens section, and a capacitor that is coupled to the one or the plurality of coil antennas in series or in parallel,
the one or the plurality of coil antennas includes:
two first wiring layers that are disposed opposite to each other with an insulating layer sandwiched therebetween; and
a connecting section that is provided inside a same layer as the insulating layer and electrically couples the two first wiring layers to each other, and
the capacitor includes two second wiring layers that are respectively provided inside same layers as the two first wiring layers.

2. The contact lens according to claim 1, wherein the one or the plurality of coil antennas is disposed along an end edge of the lens section.

3. An accessory comprising a communication section that communicates with a contact lens,
wherein the communication section includes a plurality of coil antennas having different extending directions from one another, and a capacitor that is coupled to each of the coil antennas in series or in parallel,
at least one coil antenna includes:
two first wiring layers that are disposed opposite to each other with an insulating layer sandwiched therebetween; and
a connecting section that is provided inside a same layer as the insulating layer and electrically couples the two first wiring layers to each other, and
the capacitor includes two second wiring layers that are respectively provided inside same layers as the two first wiring layers.

4. The accessory according to claim 3, wherein the accessory takes a form that does not cause a positional relationship between each of the coil antennas and the contact lens is to be determined with an azimuth direction when the accessory is worn on a body, or is to be worn on an arm, a finger, or a leg.

5. The accessory according to claim 4, wherein the accessory is a necklace, a bracelet, an earring, a finger ring, or a wristwatch.

6. An accessory comprising a communication section that communicates with a contact lens,
- wherein the communication section includes a coil antenna extending in a direction that is communicable with the contact lens when the accessory is worn on a body, and a capacitor that is coupled to the coil antenna in series or in parallel,
- at least one coil antenna includes:
  - two first wiring layers that are disposed opposite to each other with an insulating layer sandwiched therebetween; and
  - a connecting section that is provided inside a same layer as the insulating layer and electrically couples the two first wiring layers to each other, and
- the capacitor includes two second wiring layers that are respectively provided inside same layers as the two first wiring layers.

7. The accessory according to claim 6, wherein the accessory takes a form that causes a positional relationship between the coil antenna and the contact lens to be determined with an azimuth direction when the accessory is worn on a body.

8. The accessory according to claim 7, wherein the accessory is an earphone, a necklace, eyeglasses, a tiepin, a badge, a headset, a cap or a hat, a helmet, a snorkeling mask, ski goggles, a hairpiece, or a wig.

* * * * *